(12) United States Patent
Fallin et al.

(10) Patent No.: US 6,972,027 B2
(45) Date of Patent: Dec. 6, 2005

(54) SOFT TISSUE REPAIR SYSTEM

(75) Inventors: T. Wade Fallin, Hyde Park, UT (US);
M. Todd Miller, Saratoga, CA (US);
Gordon Baker, Nibley, UT (US)

(73) Assignee: Stryker Endoscopy, San Jose, CA (US)

( * ) Notice: Subject to any disclaimer, the term of this patent is extended or adjusted under 35 U.S.C. 154(b) by 397 days.

(21) Appl. No.: 10/180,901

(22) Filed: Jun. 26, 2002

(65) Prior Publication Data

US 2004/0002734 A1   Jan. 1, 2004

(51) Int. Cl.⁷ .............................................. A61B 17/04
(52) U.S. Cl. ...................................... 606/232; 606/139
(58) Field of Search ............................... 606/232, 139; 24/115 H, 115 K

(56) References Cited

U.S. PATENT DOCUMENTS

| | | | |
|---|---|---|---|
| 3,875,648 A | 4/1975 | Bone | |
| 4,144,876 A | 3/1979 | DeLeo | |
| 4,235,238 A | 11/1980 | Ogiu et al. | |
| 4,669,473 A | 6/1987 | Richards et al. | |
| 4,696,300 A | 9/1987 | Anderson | |
| 4,705,040 A | 11/1987 | Mueller | |
| 4,741,330 A | 5/1988 | Hayhurst | |
| 4,918,785 A | 4/1990 | Spinner | |
| 4,976,013 A | 12/1990 | Wax | |
| 5,041,129 A | 8/1991 | Hayhurst | |
| 5,085,661 A | 2/1992 | Moss | |
| 5,470,337 A | 11/1995 | Moss | |
| 5,601,571 A | 2/1997 | Moss | |
| 5,626,614 A | 5/1997 | Hard | |
| 5,693,060 A * | 12/1997 | Martin | 606/148 |
| 5,810,853 A * | 9/1998 | Yoon | 606/151 |
| 5,897,935 A | 4/1999 | Ellis | |
| 5,961,538 A * | 10/1999 | Pedlick et al. | 606/232 |
| 5,976,127 A | 11/1999 | Lax | |
| 6,030,007 A * | 2/2000 | Bassily et al. | 289/1.5 |
| 6,635,073 B2 * | 10/2003 | Bonutti | 606/232 |
| 2002/0019649 A1 | 2/2002 | Sikora et al. | |

* cited by examiner

Primary Examiner—Gary Jackson
(74) Attorney, Agent, or Firm—Workman Nydegger

(57) ABSTRACT

A suture anchor delivery system includes a handle having a needle extending therefrom. A suture anchor assembly is slidably received on the needle. The suture anchor assembly includes a proximal anchor, a distal anchor, and a suture extending therebetween. The suture is secured to the proximal anchor by forming a loop in the suture and passing the loop at least partially through a passageway in the proximal anchor. One end of the suture is then secured to the distal anchor. The other end of the suture is passed through the loop and terminates in a free end to selectively lock the suture against the proximal anchor. A retraction line is passed through the loop to allow a surgeon to selectively adjust the length of the suture between the two anchors and/or to selectively unlock the suture from the proximal anchor.

39 Claims, 17 Drawing Sheets

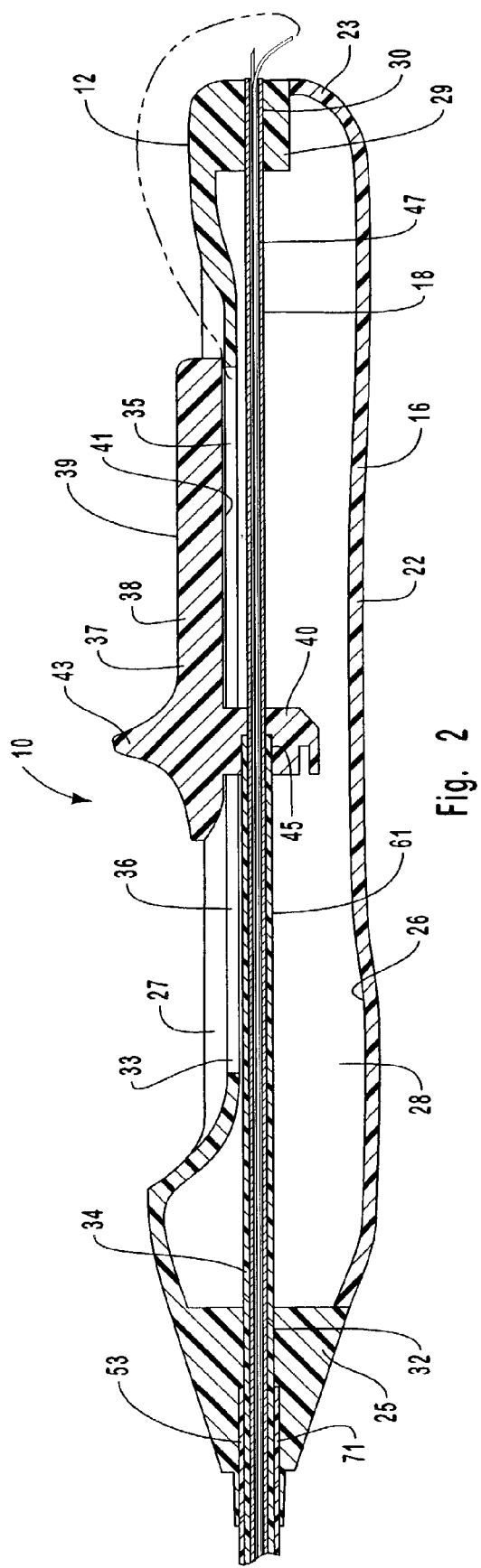
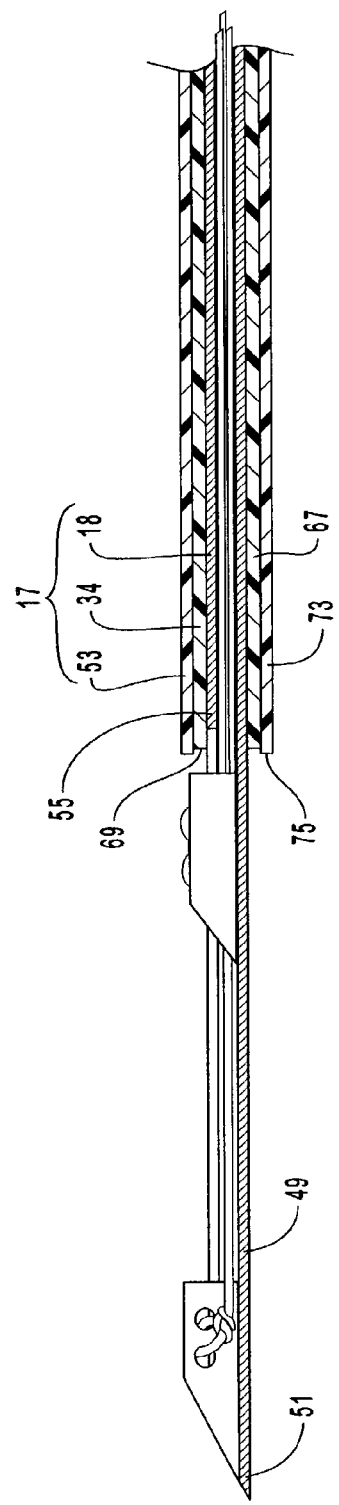
Fig. 2
Fig. 2A

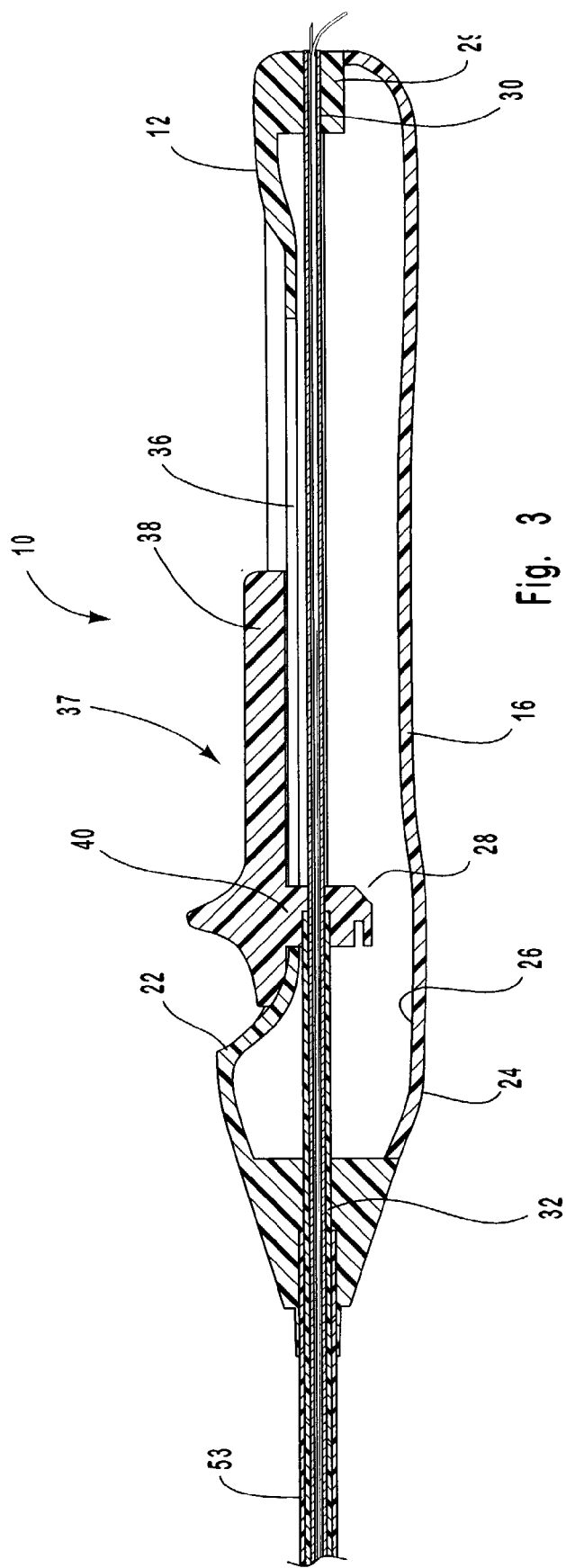
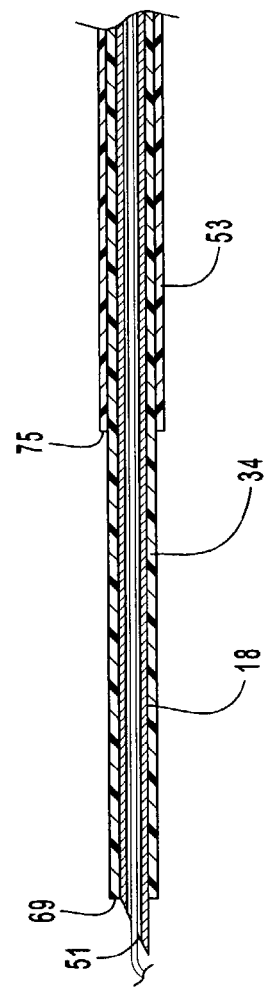
Fig. 3
Fig. 3A

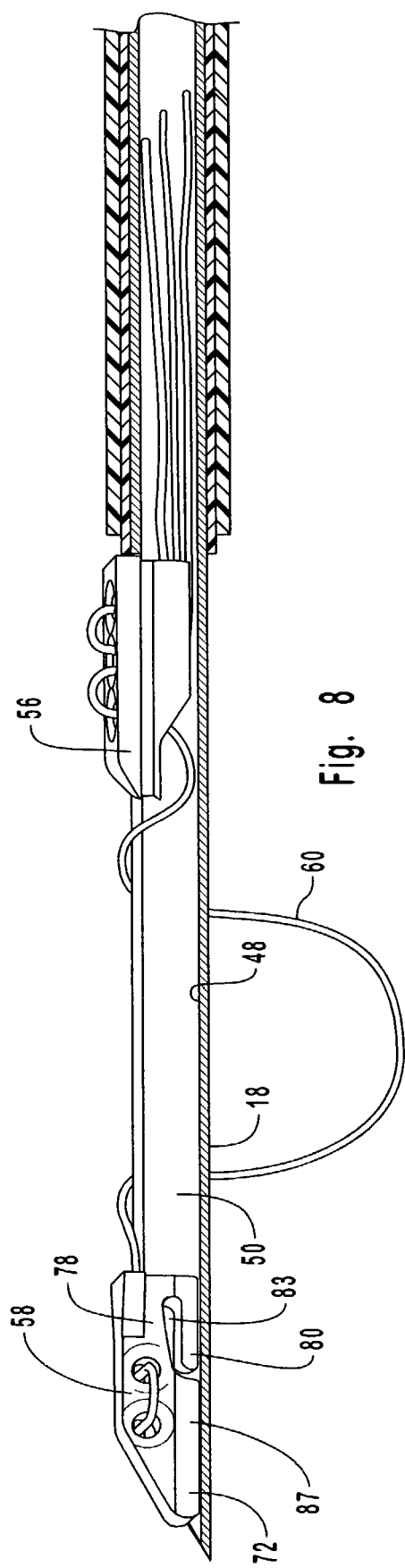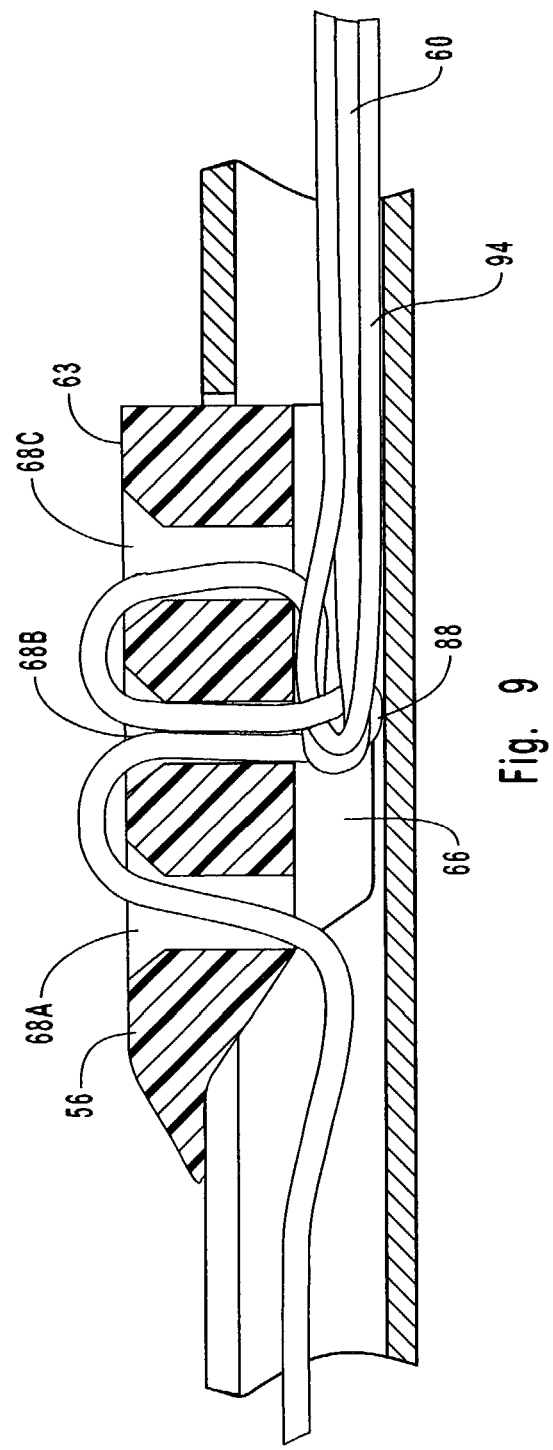

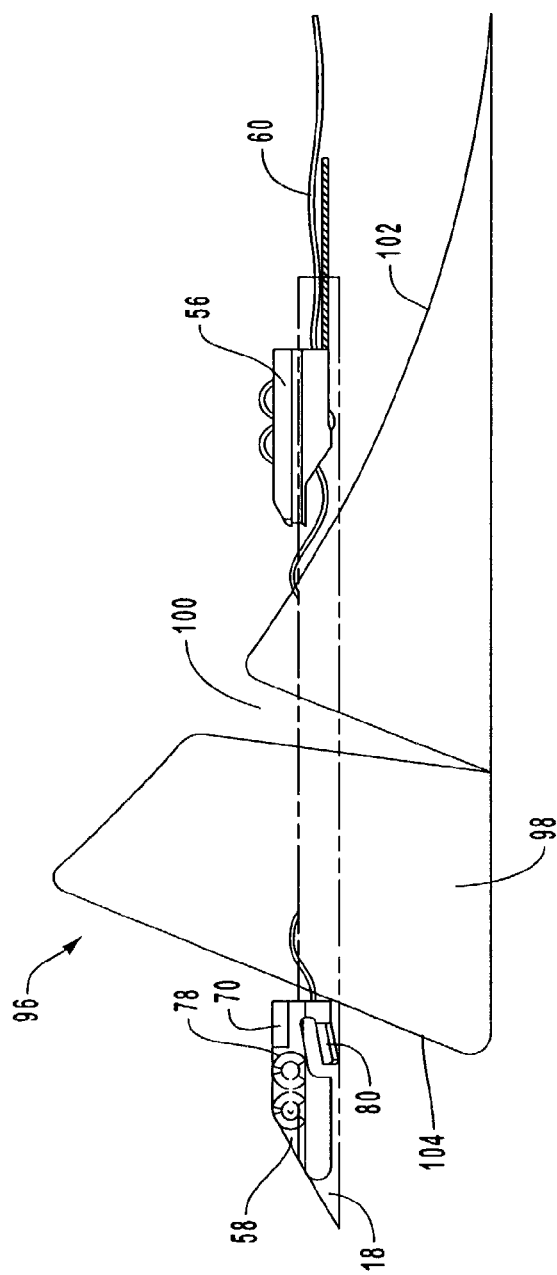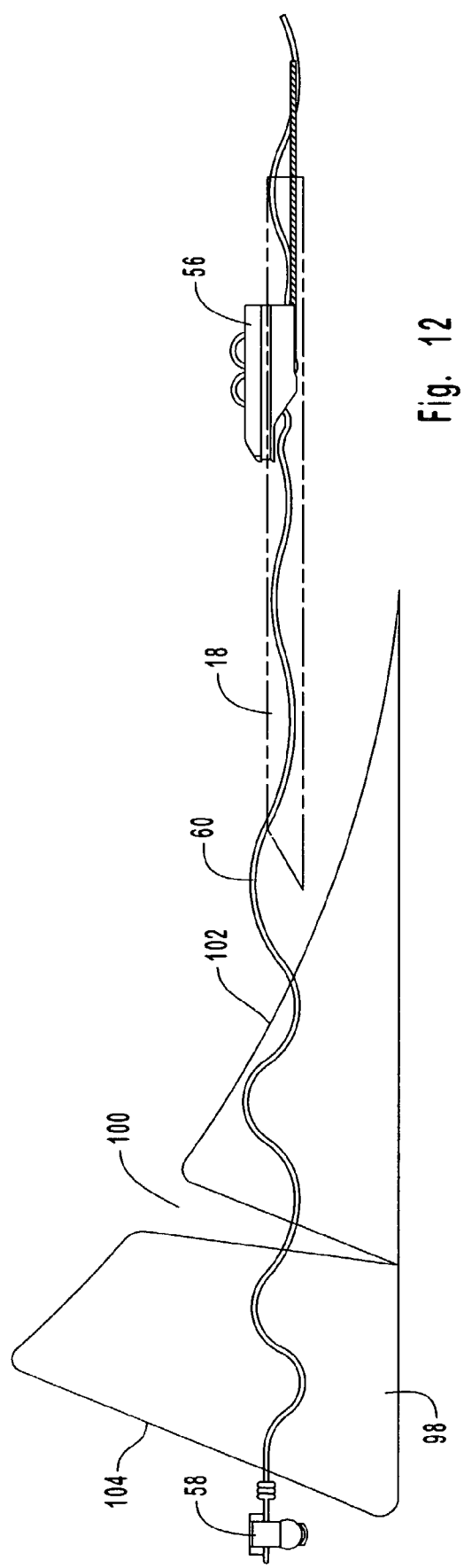

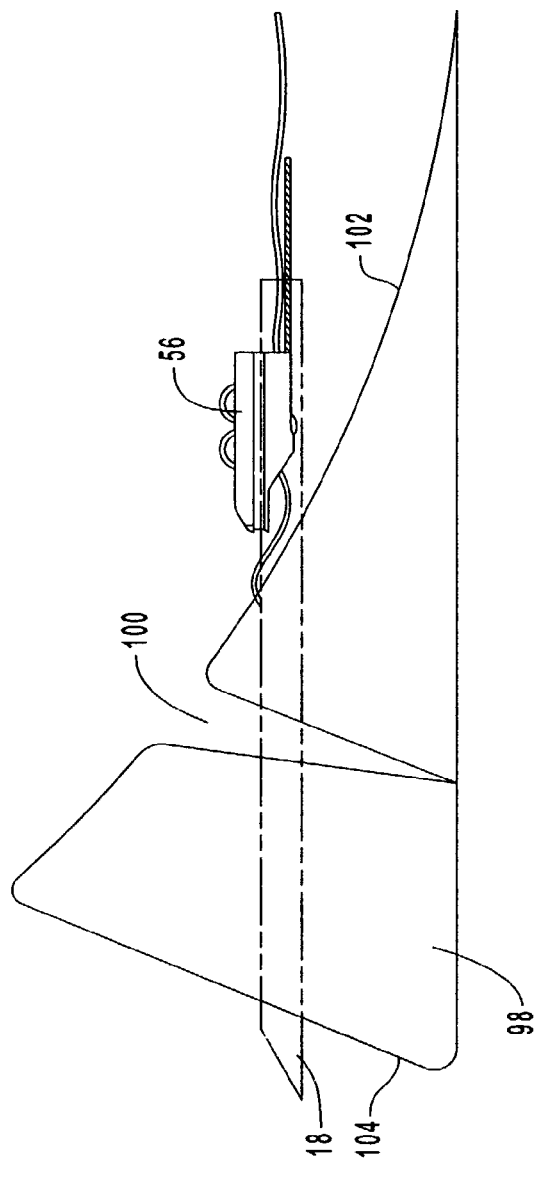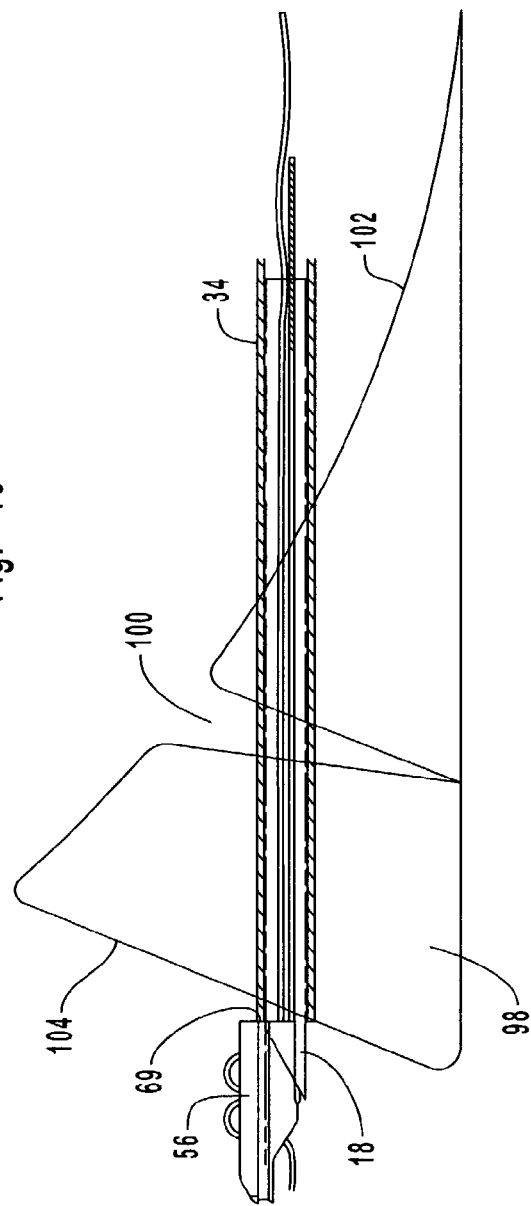

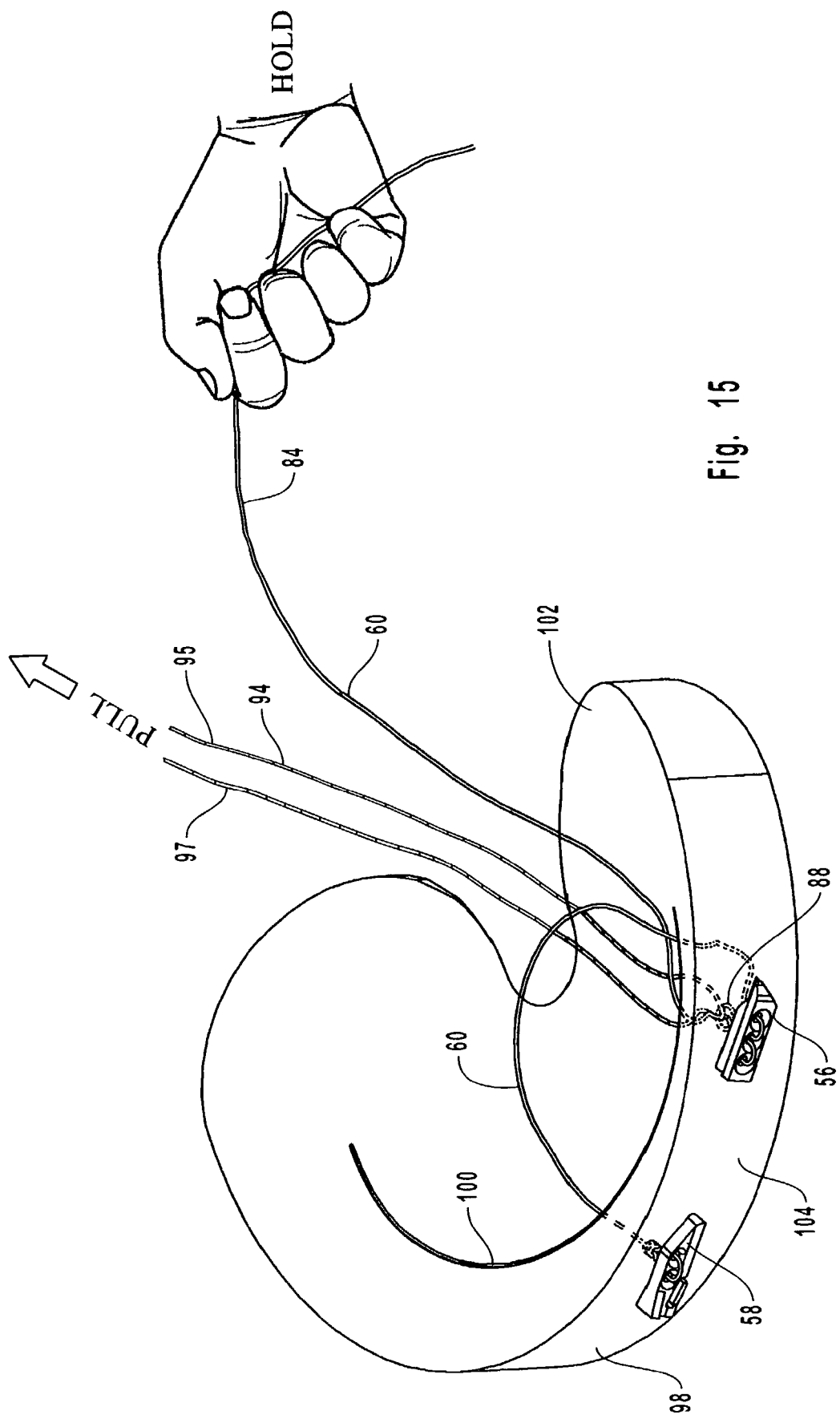

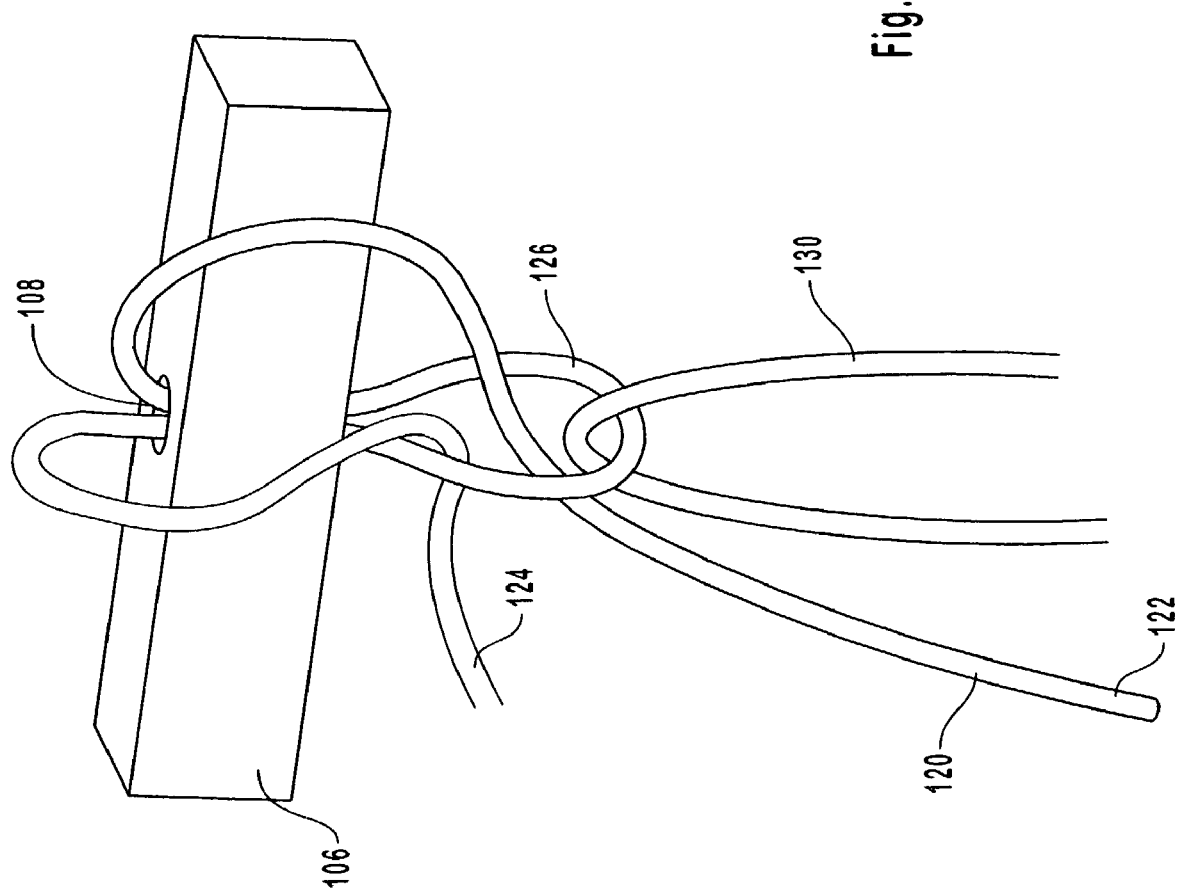

SOFT TISSUE REPAIR SYSTEM

CROSS-REFERENCE TO RELATED APPLICATIONS

Not applicable.

BACKGROUND OF THE INVENTION

1. The Field of the Invention

The present invention relates to suture anchors used for surgically repairing soft tissue, as well as instrumentation and methods for deploying such anchors.

2. The Relevant Technology

One common type of soft tissue injury is the tearing of the meniscus within the joint of the knee. The meniscus plays an important role in absorbing impact and preventing the bones of the knee joint from directly wearing against each other. Tears commonly occur from an accident or while participating in a sporting activity. Such injuries can produce continued or repeated inflammation of the knee joint and, in more extreme cases, produce binding on the knee joint, thereby preventing normal mobility.

A common surgical procedure to remedy the injury is to remove the torn portion of the meniscus through an arthroscopic procedure. Depending on how much of the meniscus is removed, however, this procedure can result in direct contact by the bones of the knee joint during normal activity. As such, the bones begin to wear, potentially creating other problems in the future.

A tear in the meniscus can be healed if the tissue bounding the tear is securely held together for a sufficiently long period of time to allow the tissue to bind together. Although a number of different pin and anchor systems have been developed for facilitating repair of a torn meniscus, each of the conventional approaches has shortcomings. Most commonly, the pin and anchor systems do not sufficiently hold the tissue together to allow healing of the tear. Another common shortcoming is that the pin or anchor systems require some structure to remain in or on the bearing surface of the meniscus. This structure is compressed between the bones of the knee joint during normal use. As such, the structure can produce wear on the meniscus and/or the bones of the knee joint.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIGS. 2 and 2A illustrate a cross-sectional side view of the suture delivery system shown in FIG. 1 with the handle in a retracted position;

FIGS. 3 and 3A illustrate a cross-sectional side view of the suture delivery system shown in FIG. 1 with the handle in an advanced position;

FIG. 8 is a side view of the suture anchor assembly of FIG. 4 with the needle in cross section;

FIG. 9 is an enlarged cross-sectional side view of the proximal anchor of the suture anchor assembly shown in FIG. 8;

FIG. 11 is a side view of the suture anchor assembly of FIG. 10 with a tip of the needle and distal anchor being passed through the soft tissue;

FIG. 12 is a side view of the assembly shown in FIG. 11 with the needle being retracted and the distal anchor positioned;

FIG. 13 is a side view of the assembly shown in FIG. 12 with the needle being passed again through the soft tissue;

FIG. 14 is a side view of the assembly shown in FIG. 13 with the proximal anchor being advanced through the soft tissue;

FIG. 15 is a perspective view of the soft tissue of FIG. 10 having both the proximal anchor and distal anchor mounted thereon;

FIGS. 19–23 are alternative embodiments of suture anchors having sutures uniquely mounted thereon for selective locking.

DETAILED DESCRIPTION OF THE PREFERRED EMBODIMENTS

Figure 1:
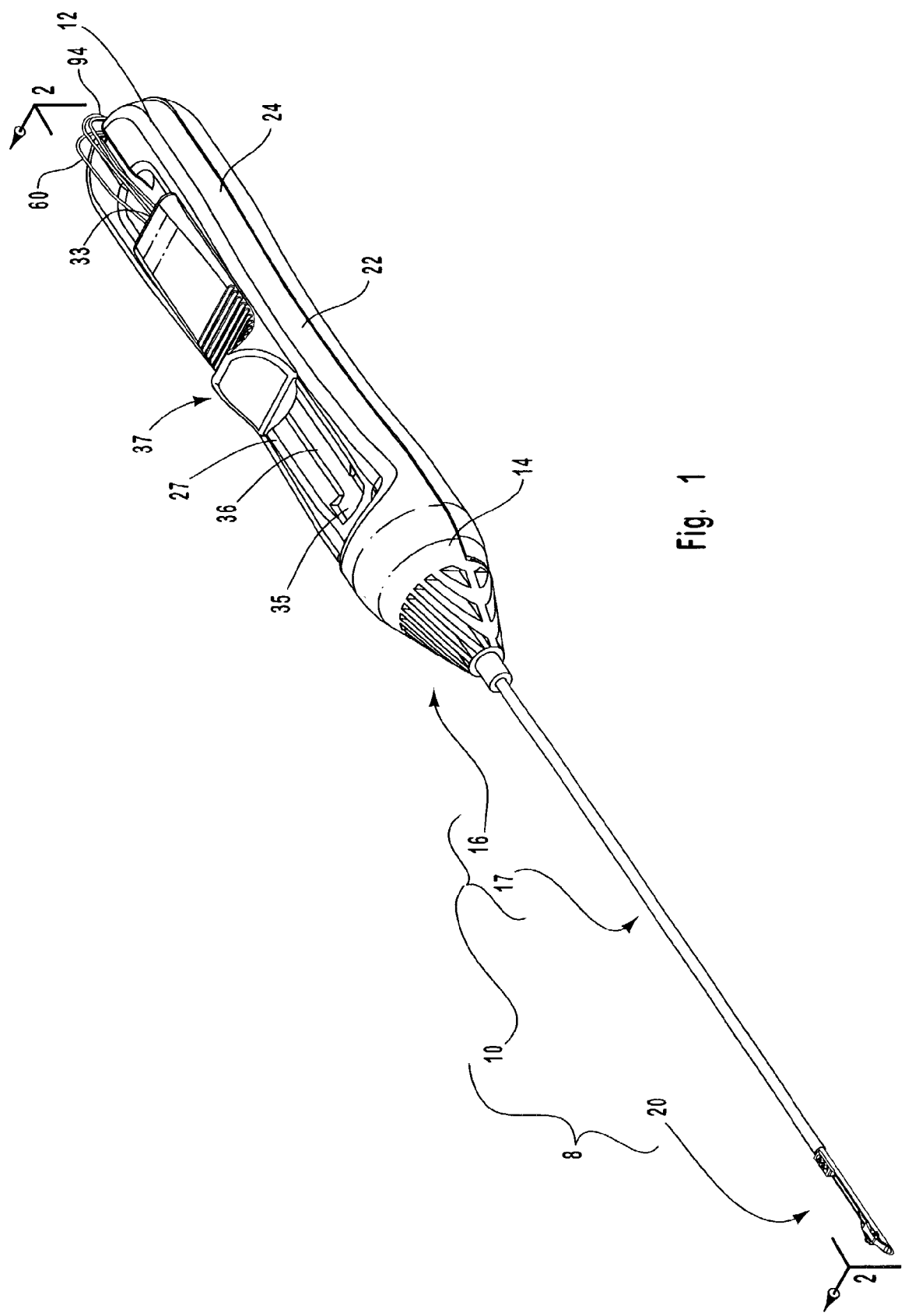
FIG. 1 is a perspective view of one embodiment of a suture delivery system of the present invention.

Depicted in FIG. 1 is one embodiment of an inventive suture delivery system 8 incorporating features of the present invention. Suture delivery system 8 comprises an insertion device 10 and a suture anchor assembly 20 disposed thereon. Suture delivery system 8 is configured for inserting suture anchors of suture anchor assembly 20 into soft tissue so as to subsequently facilitate repair of the soft tissue, such as the meniscus, tendons, ligaments, muscles, or the like. It will be appreciated, however, that suture delivery system 8 may also be used in a variety of other applications.

Insertion device 10 comprises a handle 16 having a needle assembly 17 extending therefrom. Handle 16 has an exterior surface 24 extending between a proximal end 12 and an opposing distal end 14. Although handle 16 is shown having a generally circular transverse cross section, it is appreciated that handle 16 may have any of a variety of alternative cross-sectional shapes such as, but not limited to, square, rectangular, oblong, triangular, and the like.

As shown in FIG. 2, handle 16 comprises an elongated, tubular sidewall 22 extending between a proximal end wall 23 and an opposing distal end wall 25. Handle 16 has an interior surface 26 that bounds a chamber 28. Projecting into chamber 28 from proximal end wall 23 is a support 29. It is appreciated that support 29 can be formed separate from or integral with proximal end wall 23 and can be eliminated by simply increasing the thickness of proximal end wall 23. A passageway 30 extends through proximal end wall 23 and support 29 so as to communicate with chamber 28. Similarly, a passageway 32 extends through distal end wall 25 so as to communicate with chamber 28. Passageways 30 and 32 are disposed in axial alignment.

As depicted in FIGS. 1 and 2, exterior surface 24 of handle 16 includes a top surface 27. An elongated slot 36 is oriented along the length of top surface 27 and extends through sidewall 22 so as to communicate with chamber 28. Slot 36 has a proximal end 33 and an opposing distal end 35.

A lever 37 is slidably mounted on handle 16. Specifically, lever 37 comprises a slide plate 38 having a top surface 39 and an opposing bottom surface 41. Bottom surface 41 of slide plate 38 rides against top surface 27 of handle 16. An arm 40 downwardly projects from bottom surface 41 of slide plate 38, through slot 36, and into chamber 28. A rib outwardly projects from each side of arm 40 within chamber 28 so as to retain arm 40 within chamber 28. A passageway 45 extends through arm 40 in alignment with passageways 30 and 32. Lever 37 further comprises a thumb rest 43 upwardly projecting from top surface 39 of slide plate 38. Lever 37 is selectively operable along slot 36 between a retracted distal position as shown in FIGS. 1 and 2 and an advanced proximal position as shown in FIG. 3.

As depicted in FIGS. 2 and 2A, needle assembly 17 generally comprises a needle 18, a sleeve 34 slidably disposed about a portion of needle 18, and a sheath 53 covering at least a portion of sleeve 34. Needle 18 has a proximal end 47 and an opposing distal end 49 that terminates at a sharpened distal tip 51. Proximal end 47 of needle 18 is secured within passageway 30 of support 29 by adhesive, welding, or other conventional forms of attachment. Needle 18 freely extends distally through passageway 45 of lever 37 and passageway 32 of distal end wall 25 such that distal end 49 of needle 18 freely projects distal of handle 16. In alternative embodiments, it is appreciated that needle 18 need only extend partially along the length of handle 16.

Figure 4:
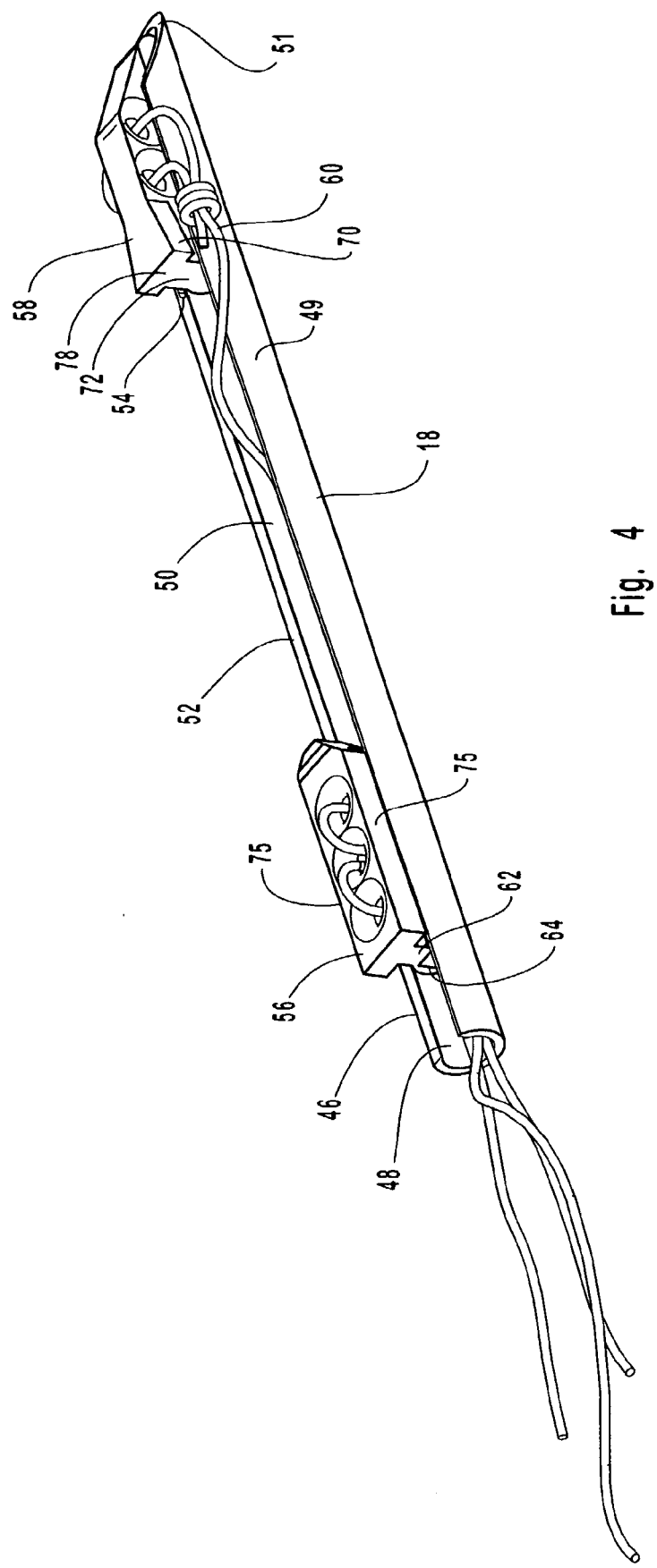
FIG. 4 is a perspective view of the suture anchor assembly of the delivery system shown in FIG. 1 mounted on a needle of the system.
Figure 5:
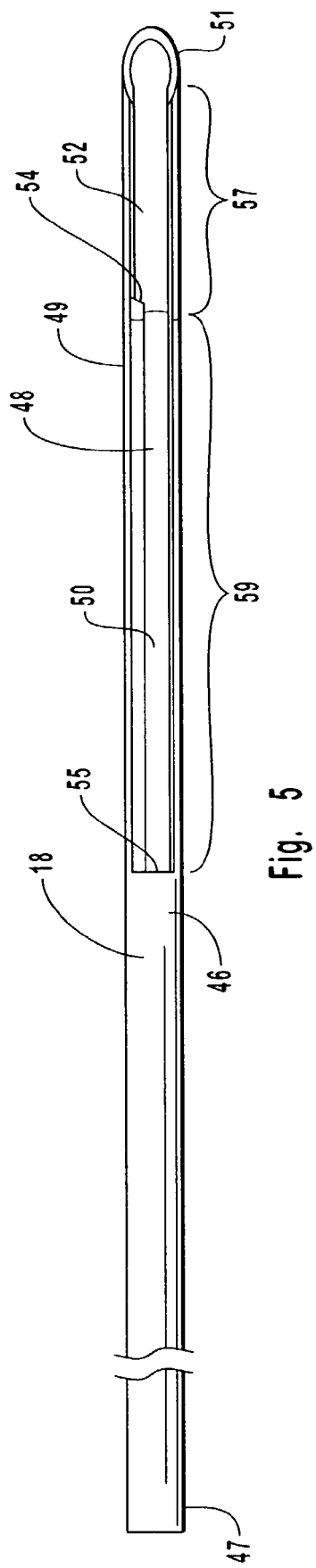
FIG. 5 is a top plan view of the needle of the delivery system shown in FIG. 1.

As shown in FIGS. 4 and 5, needle 18 comprises an exterior surface 46 and an interior surface 48 each extending between proximal end 47 and distal end 49. Interior surface 48 bounds a passage 50 extending through needle 18. A slot 52 is formed on an upper surface of needle 18 and extends between exterior surface 46 and interior surface 48. Slot 52 runs from distal tip 51 to a lip 55 formed proximal thereof. In alternative embodiments, it is appreciated that slot 52 can extend the entire length of needle 18 or can terminate at any point proximal of lip 55. As shown in FIG. 5, slot 52 comprises a wide distal portion 57 and a narrow proximal portion 59. A shoulder 54 is formed on one side of slot 52 at the intersection of portions 57 and 59. In another embodiment, shoulders can be formed on each side of slot 52 at the intersection of portions 57 and 59. The function of shoulder 54 will be discussed below in greater detail.

Figure 6:
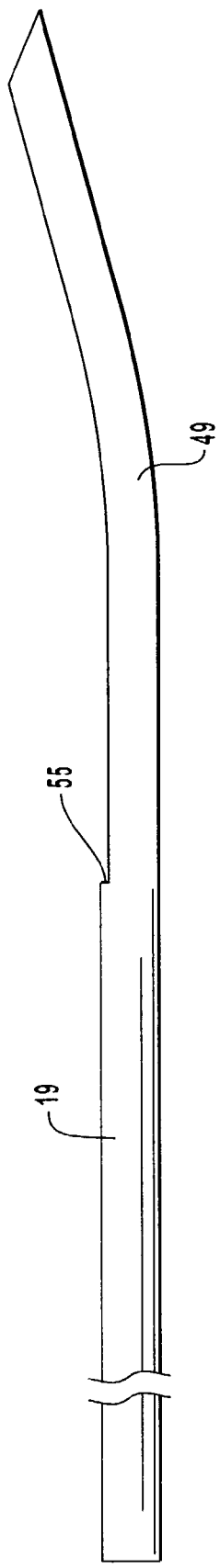
FIG. 6 is an elevated side view of an alternative embodiment of the needle shown in FIG. 5.

In the embodiment shown in FIG. 5, needle 18 is straight along its entire length. In an alternative embodiment depicted in FIG. 6, a needle 19 is shown having a distal end 49 that curves upwardly. It will be appreciated that depending on the intended use thereof, the distal end of needle 18 can be curved or bent into a variety of alternative configurations.

Returning to FIGS. 2 and 2A, sleeve 34 encircles needle 18 so as to freely slide over needle 18. Sleeve 34 extends between a proximal end 61 and an opposing distal end 67. Proximal end 61 of sleeve 34 is secured within passageway 45 of lever 37 such as by an adhesive, welding or other conventional forms of connection. Sleeve 34 extends distally through passageway 32 of handle 16 and terminates at a free distal end face 69.

Since sleeve 34 is connected to lever 37, sleeve 34 is slid between an advanced position and a retracted position as lever 37 is selectively moved between its advanced and retracted positions, For example, depicted in FIGS. 2 and 2A, lever 37 and sleeve 34 are each in their retracted proximal position. In this position, distal end face 69 of sleeve 34 is disposed proximal of the anchors of suture anchor assembly 20. In the advanced distal position depicted in FIGS. 3 and 3A, sleeve 34 slides along needle 18 such that distal end face 69 of sleeve 34 extends to or past distal tip 51 of needle 18. Lever 37 is thus operable to selectively position sleeve 34. In turn, as discussed below in greater detail, sleeve 34 facilitates placement of suture anchor assembly 20.

Needle 18 is typically made of a metal, such as stainless steel, but can also be made of plastic, composite, or other desired material. Where needle 18 is straight, sleeve 34 can be made of the same material as needle 18. Where needle 18 is curved, however, sleeve 34 is typically made of a polymeric material stiff enough to advance an anchor of suture anchor assembly 20 but flexible enough to conform to the contour of needle 18 as sleeve 34 passes over needle 18. For example, in one embodiment, sleeve 34 is comprised of polyimide or polyethertherketone.

Returning to FIGS. 2 and 2A, sheath 53 encircles sleeve 34 such that sleeve 34 is freely slideable therein. Sheath 53 includes a proximal end 71 and an opposing distal end 73 that terminates at a distal end face 75. Proximal end 71 of sheath 53 is secured within passageway 32 of handle 16 such as by an adhesive, welding, or other conventional forms of securing. In part, sheath 53 is disposed over sleeve 34 to protect sleeve 34. As discussed below, however, distal end face 75 of sheath 53 can also be positioned to function as a rearward or proximal stop for suture anchor assembly 20.

Figure 7:
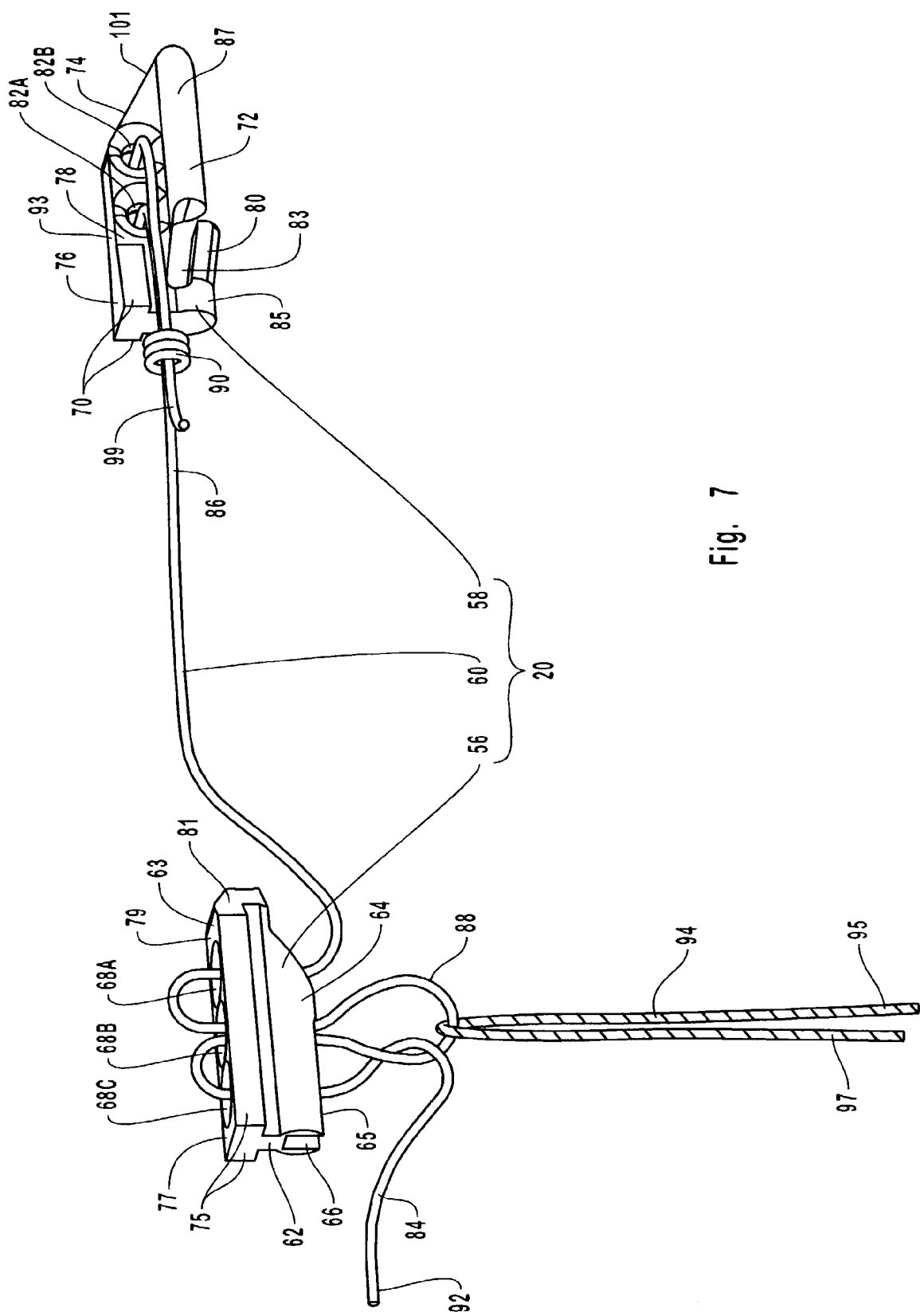
FIG. 7 is a perspective view of the suture anchor assembly shown in FIG. 4.

Depicted in FIG. 7, suture anchor assembly 20 comprises a proximal anchor 56, a distal anchor 58, and a suture 60 extending therebetween. Proximal anchor 56 has a generally elongated configuration including a top surface 63 and an opposing bottom surface 65 that each extend between a proximal end 77 and an opposing distal end 79. Distal end 79 terminates at a sharpened nose 81. An elongated channel 66 is recessed into bottom surface 65 of proximal anchor 56 and extends along the length thereof. Channel 66 is configured to receive portions of suture 60 therein. As depicted in FIG. 9, a plurality of spaced passageways 68A, 68B, and 68C extend from top surface 63 to channel 66. It is appreciated that in alternative embodiments, proximal anchor 56 may have one, two, or four or more passageways 68 extending therethrough.

Returning to FIG. 7, proximal anchor 56 is more specifically comprised of an elongated body 64 having a substantially circular transverse cross-section complementary to that of passage 50 of needle 18. Channel 66 is formed on bottom surface 65 of body 64. An elongated neck 62 upwardly projects from body 64 along the length of body 64 and terminates at top surface 63. A flange 75 outwardly projects from each side of neck 62 along the length thereof at top surface 63. In alternative embodiments, it is appreciated that flanges 75 can be eliminated or can project from only one side of neck 62. Furthermore, flanges 75 need not extend along the full length of neck 62.

Turning to FIG. 4, proximal anchor 56 is loaded onto needle 18 by sliding body 64 into passage 50 of needle 18 at distal tip 51. Proximal anchor 56 is slid proximally within passage 50 with neck 62 extending through and beyond slot 52. Body 64 has a diameter greater than the width of slot 52, thereby preventing proximal anchor 56 from unintentionally falling out through slot 52. In this regard, it is appreciated that bottom portion 64 may have a variety of alternative shapes not necessarily corresponding to the shape of needle 18. Alternatively, proximal anchor 56 may be inserted into needle 18 by snap-fit through slot 52. Flanges 75 outwardly project from neck 62 above slot 52. Depicted in FIG. 2A, proximal anchor 56 is slid proximally until proximal anchor 56 hits a stop such as distal end face 69 of sleeve 34, distal end face 75 of sheath 53, or lip 55 of needle 18.

Returning to FIG. 7, distal anchor 58 has a generally elongated configuration that extends between a proximal end 76 and an opposing distal end 74. Distal end 74 terminates at a downwardly sloping sharpened nose 101. More specifically, distal anchor 58 comprises an elongated body 72 that extends between proximal end 76 and distal end 74. Body 72 has a generally circular transverse cross-section complementary to that of passage 50 of needle 18. A notch 83 is formed through body 72 so as to divide body 72 into a proximal portion 85 and a spaced apart distal portion 87. In alternative embodiment, notch 83 need not completely divide body 72.

A flexible prong 80 projects from proximal portion 85 of body 72 into notch 83 and extends below body 72. Prong 80 can be resiliently biased into notch 83 so as to be in alignment with body 72.

An elongated neck 78 upwardly projects from body 72 along the length thereof and spans across notch 83. Neck 78 terminates at a free top surface 93. A pair of spaced apart passageways 82A and 82B transversely extend between the opposing sides of neck 78. In alternative embodiments, one or three or more passageways 82 can be formed on distal anchor 58. Furthermore, passageways 82 can extend at a variety of other orientations. Positioned proximal of passageways 82, a wedged shaped flange 70 outwardly projects from each side of neck 78 at top surface 93. In alternative embodiments, flanges 70 can be eliminated or project from only one side of neck 78.

As shown in FIG. 4, distal anchor 58 is loaded onto needle 18 by sliding body 72 into passage 50 of needle 18 at distal tip 51. Distal anchor 58 is slid proximally within passage 50 with neck 78 extending through and beyond slot 52. Body 72 has a diameter greater than the width of slot 52, thereby preventing distal anchor 58 from unintentionally falling out through slot 52. In this regard, it is appreciated that body 72 may have a variety of alternative shapes not necessarily corresponding to the shape of passage 50 of needle 18. Furthermore, distal anchor 58 may be inserted into needle 18 by snap-fit through slot 52. Flanges 70 outwardly project from neck 78 above slot 52. Distal anchor 58 is slid proximally until distal anchor 58 hits against shoulder 54 of needle 18. In this regard, neck 78 of distal anchor 58 is slightly wider than neck 62 of proximal anchor 56.

As depicted in FIG. 8, as body 72 of distal anchor 58 is slid into passage 50 of needle 18, prong 80 is compressed into notch 83 so as to resiliently bias against interior surface 48 of needle 18. As a result, prong 80 frictionally secures distal anchor 58 within needle 18 so as to preclude distal anchor 58 from unintentionally sliding out of passage 50. In this regard, it is appreciated that prong 80 can also project from distal portion 87 of body 72 or from neck 78. Furthermore, prong 80 need not project below body 72 but can project from the sides thereof. In addition, prong 80 can be divided.

As shown in FIG. 7, proximal anchor 56 and distal anchor 58 are secured together by suture 60. As used in the specification and appended claims, the term "suture" is broadly intended to include any type of flexible line but typically comprises medical grade suture. Suture 60 comprises a proximal end 84 that terminates at a free end 92 and an opposing distal end 86 that terminates at a distal tip 99. Distal end 86 of suture 60 is secured to distal anchor 58 by passing distal tip 99 through passageway 82A and then passing distal tip 99 back through passageway 82B. Portions of suture 60 proximal and distal of passageways 82A and 82B are then secured together by way of a knot 90.

It is appreciated that suture 60 can be secured to distal anchor 58 in a vast number of different ways. By way of example and not by limitation, suture 60 can be loop through a single passageway and then tied to itself. Alternatively, distal tip 99 can be passed through a single passageway. A large knot can then be formed at distal tip 99, the knot being sufficiently large to preclude distal tip 99 from passing back through the passageway. In yet other embodiments, distal end 86 of suture 60 can be secured to distal anchor 58 by an adhesive, clamp, being integrally molded therewith, or any number of other conventional fastening techniques.

Suture 60 extends from distal anchor 58 to proximal anchor 56. At proximal anchor 56, suture 60 extends from bottom surface 65 up through passageway 68A. A loop 88 is then formed on suture 60. As used in the specification and appended claims, the term "loop" is defined as a curving or doubling of a line so as to form a closed or partly open curve within itself through which another line can be passed or into which a hook may be hooked. Loop 88 is passed down through passageway 68B. Suture 60 proximal of loop 88 then passes down through passageway 68C where it then passes through loop 88.

A retraction line 94 is passed through loop 88 of suture 60 such that opposing ends 95 and 97 of retraction line 94 project from loop 88. Retraction line 94 comprises a suture or any other form of flexible line. It is appreciated that in one embodiment, retraction line 94 can comprise the proximal end of suture 60. Furthermore, retraction line 94 can be formed into a continuous loop. Retraction line 94 is positioned such that by simultaneously pulling on opposing ends 95 and 97, tension can be applied to loop 88 in a direction away from proximal anchor 56.

In the above assembled configuration, pulling on free end 92 of suture 60 selectively locks suture 60 to proximal anchor 56. Specifically, as free end 92 of suture 60 is tensioned, loop 88 begins to be retracted into passageway 68B. Passageway 68B has a diameter large enough to receive loop 88 but too small to permit loop 88 and the portion of suture 60 passing therethrough to be pulled through passageway 68B. For example, in one embodiment where suture 60 is a size 0 suture having a diameter in a range from about 0.013 inches to about 0.016 inches, passageway 68B is circular and has a diameter of about 0.25 inches. Accordingly, as the end of loop 88 begins to enter passageway 68B at the point were suture 60 passes therethrough, the overlapping suture 60 locks by a secure wedged frictional engagement against or within the opening to passageway 68B of proximal anchor 56. To release this locked engagement, retraction line 94 is pulled on which draws loop 88 away from passageway 68B, thereby releasing the locked engagement with proximal anchor 56. As will be discussed below in greater detail, by selectively drawing on proximal end 84 of suture 60 and retraction line 94, any slack in suture 60 between suture anchors 56 and 58 can be removed. Suture 60 can then be locked to proximal anchor 56.

In the loaded state shown in FIG. 8, anchors 56 and 58 are mounted on needle 18 as previously discussed. Due to the required operating slack, suture 60 extending between anchors 56 and 58 typically extends outside of passage 50 of needle 18. In contrast, as shown in FIGS. 8 and 9, suture 60 and retraction line 94, after passing through loop 88, travel within channel 66 of proximal anchor 56. After exiting channel 66, as shown in FIG. 2, suture 60 and retraction line 94 continue traveling proximally with passage 50 of needle 18 and exit therefrom at proximal end 12 of handle 16. If desired, as shown in FIG. 1, the free end of suture 60 and retraction line 94 can be inserted into the proximal end of slot 36 on handle 16. In the retracted proximal position, lever 37 biases the free ends of suture 60 and retraction line 94 against handle 16 so as to hold suture 60 and retraction line 94 in place. As lever 37 is advanced into the distal position, the free ends of suture 60 and retraction line 94 are released by lever 37 for selective removal from insertion device 10.

Referring now to FIGS. 10–18, the operation of insertion device 10 will now be described. It is understood that for FIGS. 10–14, while only needle 18 and suture anchor assembly 20 are shown, the entire insertion device 10 is being applied. It is also appreciated that before insertion device 10 is used, suture 60 is secured to proximal anchor 56 and distal anchor 58 and the entire suture anchor assembly 20 is loaded on needle 18 as described above.

Figure 10:
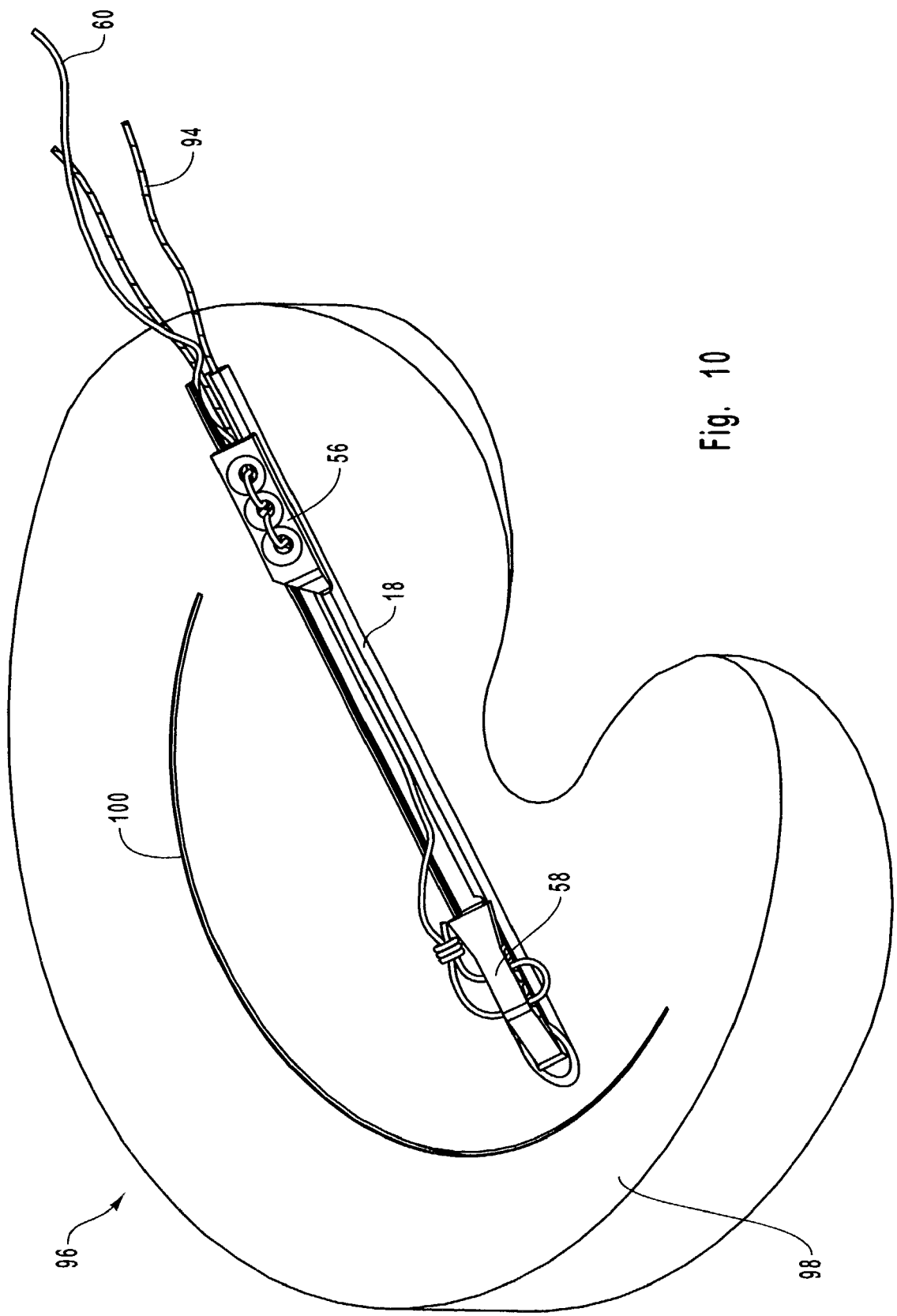
FIG. 10 is a perspective view of the suture anchor assembly of FIG. 8 positioned to be inserted into a torn meniscus.

FIG. 10 depicts an exemplary soft tissue site 96 in need of repair. In this example, a meniscus 98 is shown having a tear 100. Meniscus 98 comprises cartilage lying between the joint surfaces of the femur and the tibia. As shown in FIG. 11, meniscus 98 has a substantially triangular transverse cross-section having an inside surface 102 and an outside surface 104. Insertion device 10 is positioned to penetrate meniscus 98 from inside surface 102.

Specifically, needle 18 penetrates inside surface 102 of meniscus 98, passes through tear 100, and exits through outside face 104. Needle 18 is advanced to the extent that all of distal anchor 58 extends past outside face 104 of meniscus 98. The soft tissue of meniscus 98 sufficiently encloses around needle 18 such that as needle 18 is retracted from meniscus 98, the exposed neck 78 and flanges 70 catch on outside face 104 of meniscus 98. Distal anchor 58 is thus dislodged from needle 18 by overcoming the resistance force of prong 80 and sliding distally off of needle 18.

As shown in FIG. 12, after needle 18 is retracted from meniscus 98, distal anchor 58 is disposed on outside surface 104 of meniscus 98. Because of the way distal anchor 58 is secured to suture 60 (described above with reference to FIG. 7), distal anchor 58 generally rotates so that the elongated side of distal anchor 58 is biased against outside face 104 of meniscus 98. This orientation helps ensure that distal anchor 58 does not unintentionally pass through the puncture formed by needle 18.

Proximal anchor 56 is now secured to meniscus 98 at a short distance from distal anchor 58. Specifically, as shown in FIG. 13, needle 18 is placed on inside surface 102 of meniscus 98 at a point along tear 100 spaced apart from the initial insertion of needle 18. Needle 18 is then passed through inside surface 102, tear 100 and outside surface 104.

As depicted in FIG. 14, once needle 18 is properly positioned, lever 37 on handle 16 is advanced from the retracted proximal position to the advanced distal position. In so doing, sleeve 34 is distally advanced. Distal end face 69 of sleeve 34 biases against proximal anchor 56 and distally advances proximal anchor 56 through meniscus 98 along needle 18. Sleeve 34 continues to advance until proximal anchor 56 is released from needle 18 beyond outside surface 104 of meniscus 98. Alternatively, sleeve 34 need only advance proximal anchor 56 beyond outside surface 104 of meniscus 98. Proximal anchor 56 can then be removed from needle 18 by simply withdrawing needle 18 back through meniscus 98. In yet another alternative, sleeve 34 can function to initially advance proximal anchor 56 to the distal end of needle 18. Proximal anchor 56 can then be placed using the same method as discussed above with regard to distal anchor 58.

With needle 18 removed, proximal anchor 56 is disposed on outside surface 104 of meniscus 98. Because of the way proximal anchor 56 is secured to suture 60 (described above with reference to FIG. 7), proximal anchor 56 will generally rotate so that the elongated bottom surface 65 of proximal anchor 56 is biased against outside surface 104 of meniscus 98 (FIG. 15). Again, this orientation helps ensure that proximal anchor 56 does not pass through the puncture formed by needle 18.

FIG. 15 shows both proximal anchor 56 and distal anchor 58 disposed on outside surface 104 of meniscus 98. After needle 18 is retracted from meniscus 98, insertion device 10 is removed from the operating environment. In so doing, suture 60 and retraction line 94 are withdrawn out of needle 18 so as to freely extend outside of the body of the patient. In one embodiment, suture 60 and retraction line 94 can be different colors or have different markings thereon so as to be discernable therebetween.

Once proximal anchor 56 and distal anchor 58 are positioned, the length of suture 60 between proximal anchor 56 and distal anchor 58 is adjusted. Generally, extra slack is provided in the length of suture 60 between proximal anchor 56 and distal anchor 58 to ensure easy placement of anchors 56 and 58. Once anchors 56 and 58 are placed, however, the extra slack must be removed so that suture 60 holds tear 100 sufficiently tightly closed to ensuring healing thereat.

Figure 16:
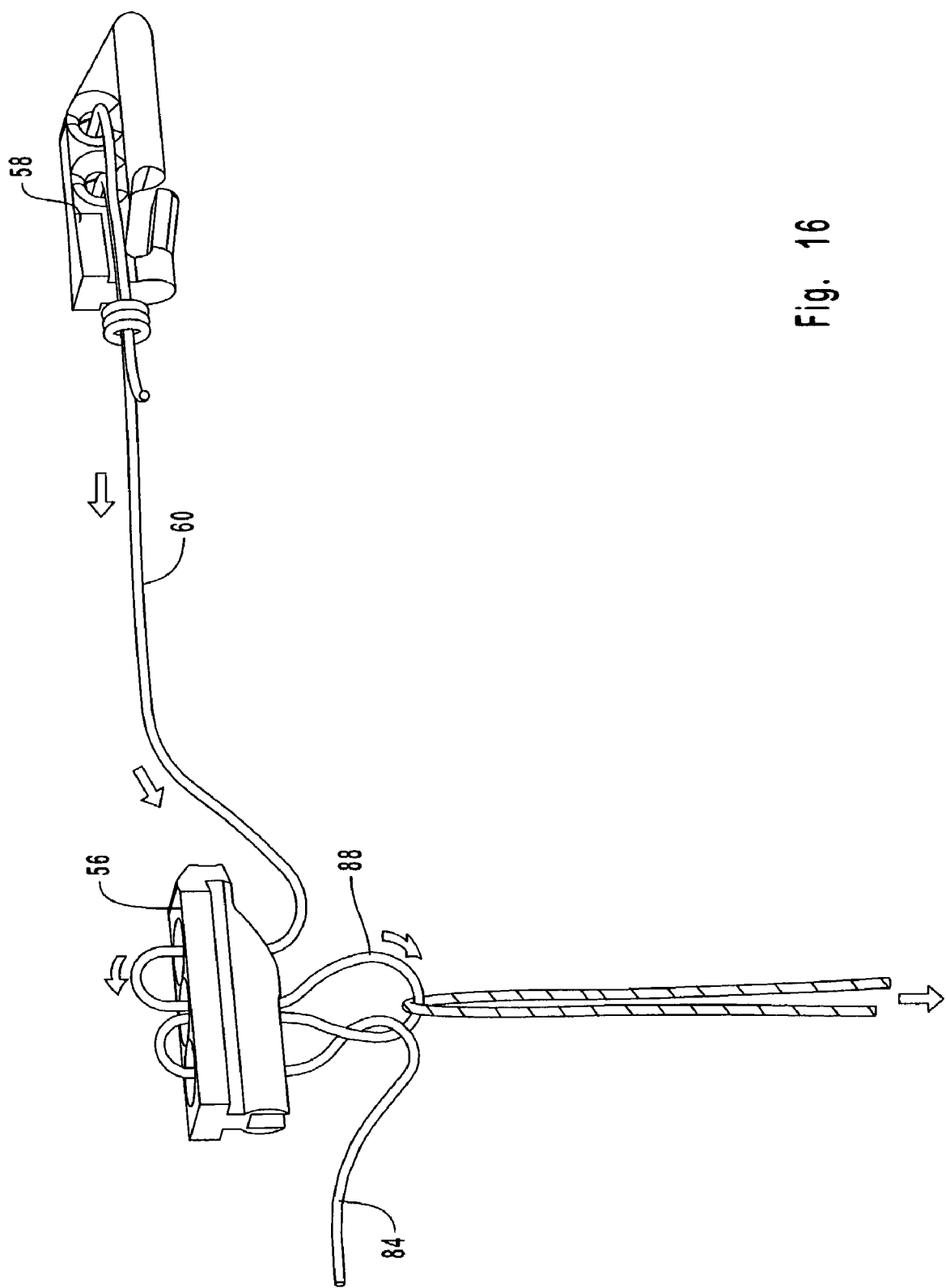
FIG. 16 is a perspective view of the proximal and distal anchor of FIG. 15 with slack from the suture extending therebetween being moved to the loop.

With reference to FIG. 15, to remove the slack in suture 60 between anchors 56 and 58, the surgeon holds the exposed proximal end 84 of suture 60 taut. The surgeon then simultaneously pulls back on both opposing free ends 95 and 97 of retraction line 94, thereby pulling on loop 88 of suture 60. As depicted in FIG. 16, because proximal end 84 of suture 60 is held taut, loop 88 enlarges under the tension of retraction line 94 by drawing in slack from between anchors 56 and 58.

Figure 17:
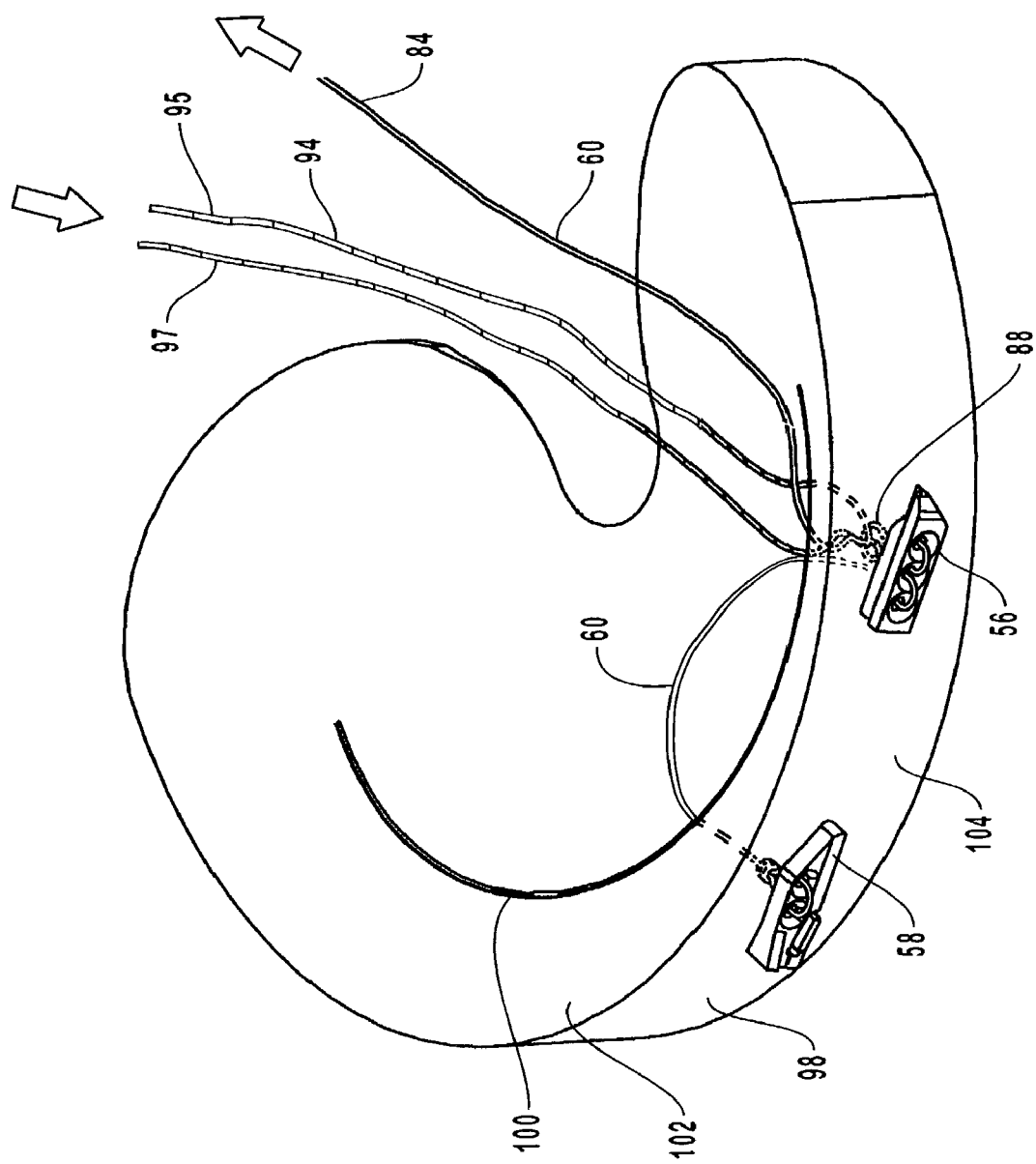
FIG. 17 is a perspective view of the soft tissue of FIG. 15 with slack in the loop of the suture being removed through the proximal end of the suture.

In turn, as depicted in FIG. 17, to remove the slack from loop 88, proximal end of 84 of suture 60 is pulled while retraction line 94 is slowly released at a complementary rate. If required, the above process is repeated until all of the slack is removed from between anchors 56 and 58.

As long as retention line 94 remains in loop 88, it is possible to selectively unlock suture 60 from proximal anchor 56. To do so, the surgeon simply applies tension to retention line 94 to loosen loop 88. The surgeon can then increase or decrease the slack in suture 60. Thus, retention line 94 allows a surgeon to make any necessary readjustments to the length of suture 60 before finally locking suture 60.

Figure 18:
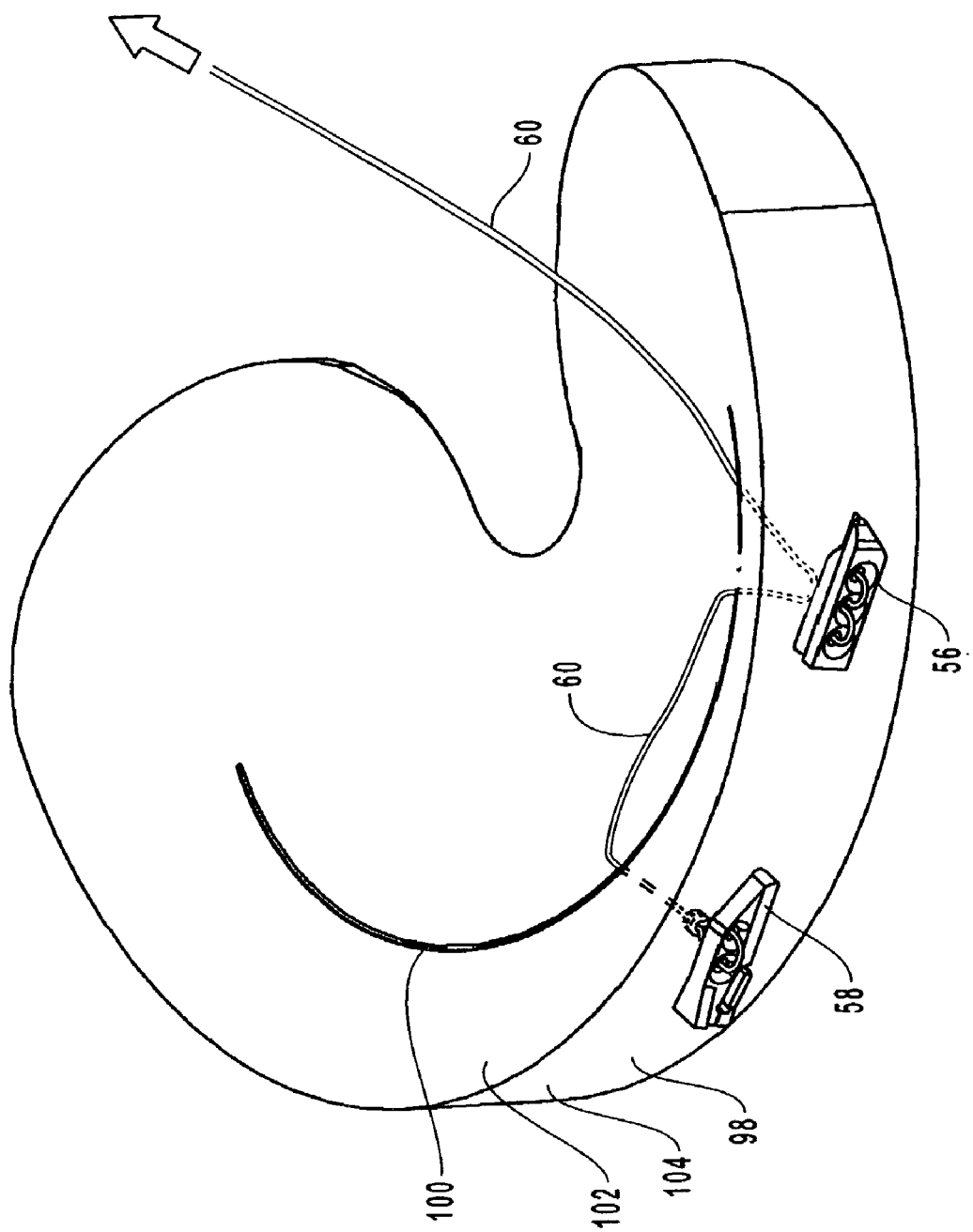
FIG. 18 illustrates a perspective view of the soft tissue of FIG. 17 having the suture locked on the proximal anchor.

As shown in FIG. 18, when the desired length of suture 60 between proximal anchor 56 and distal anchor 58 is achieved, retraction line 94 is removed from loop 88 by pulling on one of free ends 95 or 97 thereof. Exposed proximal end 84 of suture 60 is then tensioned so as to securely lock suture 60 to proximal anchor 56 as previously discussed. Suture 60 is then clipped proximal of proximal anchor 56 and removed.

The methods and apparatuses of the present invention may be applicable in a wide variety of surgical applications, not limited to the example of the meniscal repair described above. Furthermore, it will be appreciated that a single anchor or more than two anchors may be utilized without departing from the scope of the present invention. For example, suture anchor delivery system 10 may be used to employ a series of anchors within a soft tissue site. That is, a plurality of anchors may be slidably received in needle 18. Each anchor can be advanced to the distal end of needle 18 and then inserted as described above.

It is also appreciated that suture anchor assembly 20 or a discrete suture anchor thereof can be used independently of insertion device 10. For example, arthroscopic or other conventional procedures can be used to manually stitch soft tissue using a suture. Once the stitching is completed, the suture can be secured in place by use of a suture anchor described herein.

Set forth below in FIGS. 19–22 are a number of alternative configurations for securing a suture to a suture anchor. It is appreciated that these configurations can be implemented into suture anchors 56 and/or 58 or can be used independently thereof. Like elements between the various embodiments will be identified by like reference characters.

Figure 19:
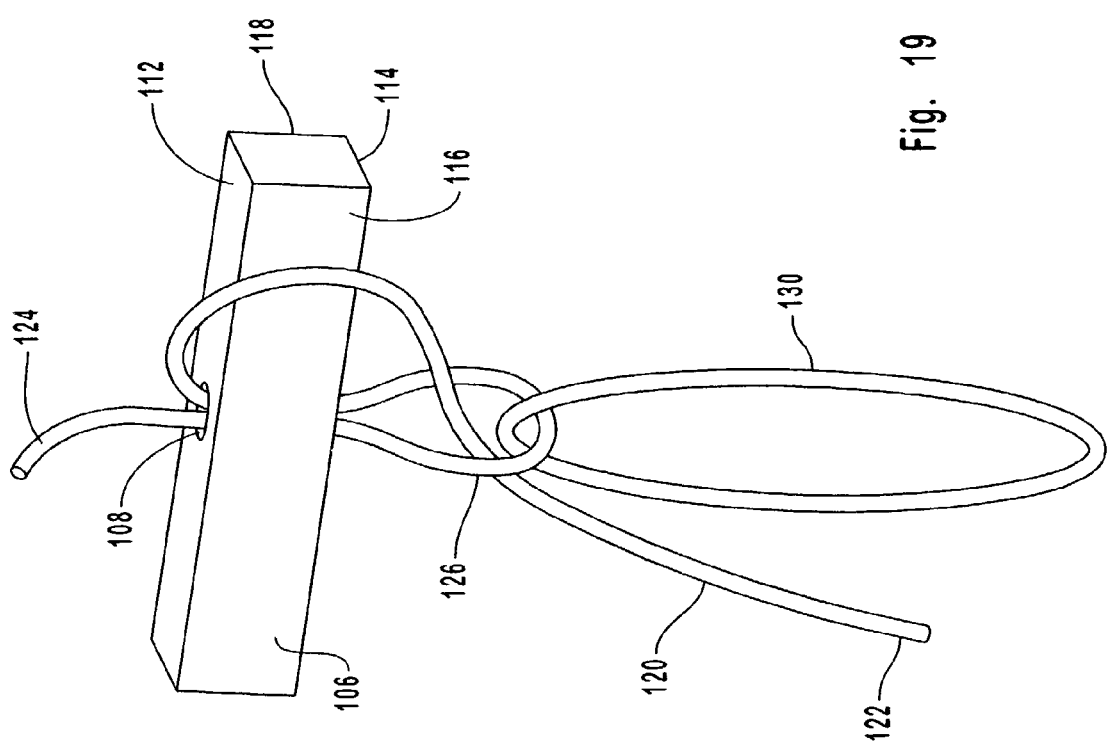

Depicted in FIG. 19 is a suture anchor 106. While anchor 106 is shown as a rectangular block, it will be appreciated that anchor 106 may have any desired configuration depending on the particular application. For example, anchor 106 can have a circular, triangular, elliptical, or any other polygonal or irregular transverse cross section. Anchor 106 can also have threads, barbs, or other fixation structure that are well known in the art for securing anchor 106 to bone. Furthermore, anchor 106 can be uniquely configured for attachment with an insertion tool. Anchor 106 comprises a top surface 112 and an opposing bottom surface 114 each extending between a front face 116 and an opposing back face 118. A single passageway 108 extends through anchor 106 from top surface 112 to bottom surface 114.

A suture 120 is provided having a proximal end 122 and an opposing distal end 124. A portion of suture 120 is formed into a loop 126. Loop 126 is passed through passageway 108 so as to project beyond bottom surface 114. Proximal end 122 of suture 120 is then passed through loop 126. A retraction line 130 also passes through loop 126. Although retraction line 130 is depicted as a continuous loop, retraction line 130 can also comprise a linear line that is looped through loop 126.

By holding one of proximal end 122 or distal end 124 taut and then pulling on the other, loop 126 begins to retract into passageway 108. This retraction continues until the overlapping sections of suture 120 at loop 126 lock with anchor 106 by a secure wedged frictional engagement against or within the opening to passageway 108 of anchor 106. If desired, an enlarged concentrically disposed recess bore can be formed at the opening of passageway 108. In this embodiment, the overlapping sections of suture 120 are received within the recess bore before locking against the constricted portion of passageway 108.

As with proximal anchor 56 previously discussed, retraction line 130 facilitates selective unlocking of the suture 120 from anchor 106. Retraction line 130 also enables selective removal or addition of slack from or to either proximal end 122 or distal end 124 of suture 120. Once suture 120 is positioned and/or locked at the desired location, retraction line 130 can be removed by being pulled through loop 126.

Figure 20:
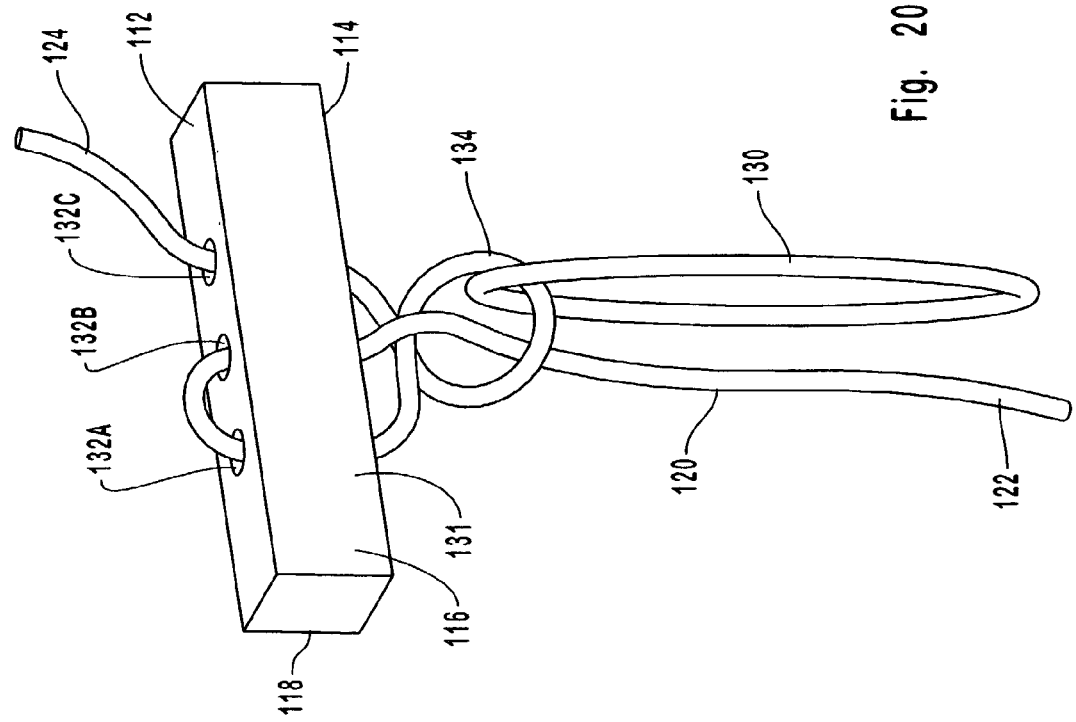

Depicted in FIG. 20 is a suture anchor 131 having a plurality of passageways 132A, 132B, and 132C each extending between top surface 112 and bottom surface 114. Suture 120 extends through anchor 131. Specifically, beginning with distal end 124, suture 120 passes down through passageway 132C. A portion of suture 120 is then coiled over itself so as to form a closed loop 134 below bottom surface 114. Proceeding proximally, suture 120 then extends up through passageway 132A and then down through passageway 132B. Suture 120 then passes through closed loop 134. Retraction line 130 also passes through loop 134.

By pulling on end 122 and/or end 124 of suture 120, loop 134 constricts about the portion of suture 120 extending therethrough, thereby locking suture 120 to suture anchor 131. Retraction line 130 enables selective expansion of loop 134 so as to unlock suture 120 from anchor 131 and to enable selective adjustment of slack in suture 120.

Figure 21:
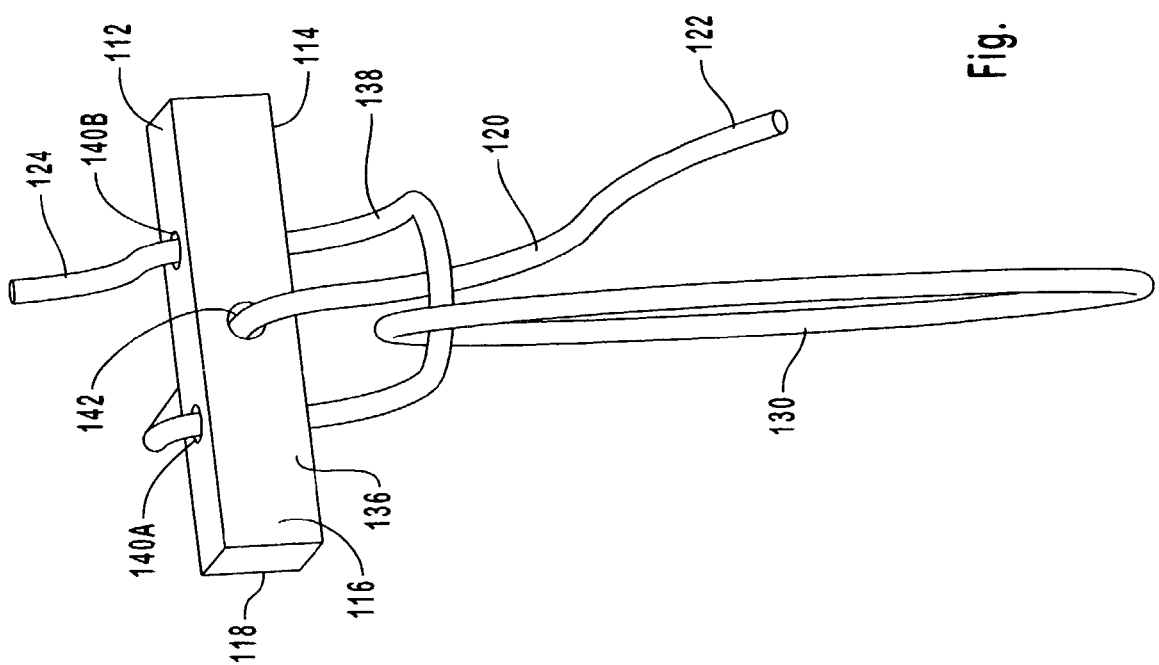

Depicted in FIG. 21 is a suture anchor 136. A pair of spaced apart passageways 140A and 140B extend between top surface 112 and bottom surface 114. A passageway 142 extends between front face 116 and back face 118. Beginning at distal end 124, suture 120 passes down through passageway 140B and then back up through passageway 140A. As such, the portion of suture 120 between passageways 140A and 140B is formed into a loop 138. Proceeding proximally, suture 120 then extends from back face 118 through passageway 142 and then through loop 138. Retraction line 130 also passes through loop 138.

By pulling on end 122 and/or end 124 of suture 120, loop 138 retracts into passageways 140A and/or 140B until the remaining portion of loop 138 securely biases the portion of suture 120 passing therethrough against the exterior surface of suture anchor 136, thereby securely locking suture 120 to suture anchor 136. Again, retraction line 130 enables selective expansion of loop 138 so as to unlock suture 120 from anchor 136 and to enable selective adjustment of slack in suture 120.

Figure 22:
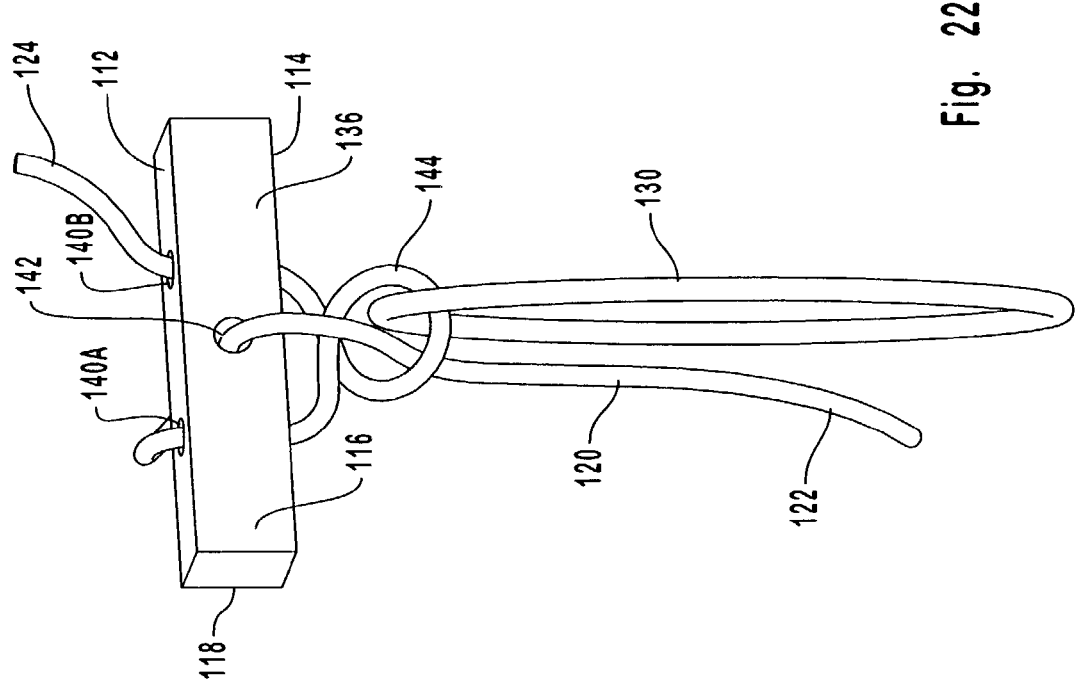

Depicted in FIG. 22, suture anchor 136 is again shown having suture 120 passing therethrough in substantially the same fashion as discussed above with regard to FIG. 21. The primary distinction is that loop 138 of FIG. 21 has been coiled in FIG. 22 into a closed loop 144. Proximal end 122 of suture 120 and retraction line 130 both pass through closed loop 144. In this embodiment, as with the embodiment depicted in FIG. 20, by pulling on end 122 and/or end 124 of suture 120, loop 144 constricts about the portion of suture 120 extending therethrough, thereby locking suture 120 to suture anchor 136. Retraction line 130 enables selective expansion of loop 144 so as to unlock suture 120 from anchor 136 and to enable selective adjustment of slack in suture 120.

Finally, depicted in FIG. 23 is suture anchor 106 having suture 120 passing therethrough in substantially the same fashion as previously discussed with regard to FIG. 19. The one distinction is that in this embodiment both proximal end 122 and distal end 124 of suture 120 pass through loop 126 to facilitate locking of suture 120 to suture anchor 106. It is appreciated that in each of the disclosed embodiment, the proximal end, distal end, or both ends of the suture can be passed through the loop formed on the suture to facilitate locking with the corresponding anchor.

It is appreciated that the retractions lines disclosed herein can also be used for selectively unlocking sutures secured on other configurations of suture anchors. For example, U.S. Pat. No. 5,693,060 discloses suture anchors having a suture selectively locked thereon. A retraction line can be passed through loop 24 of the disclosed sutures to selectively unlock the suture and to adjust slack therein. For purposes of disclosure, columns 4–9 of U.S. Pat. No. 5,693,060 and all of the drawings thereof are hereby incorporated by reference. Other alternative suture anchors that can also be used in association with the present invention are disclosed in United States Publication No. US 2002/0019649 A1, published Feb. 14, 2002. For purposes of disclosure, paragraphs [0101]–[0206] of United States Publication No. US 2002/0019649 A1 and all of the drawings thereof are hereby incorporated by reference.

The various anchors of the present invention can be made in a variety of different ways using a variety of one or more different materials. By way of example and not by limitation, the various anchors can be made from medical grade bioabsorbable or non-absorbable materials. Examples of bioabsorbable materials include homopolymers and copolymers of lactide, glycolide, trimethylene carbonate, caprolactone, and p-dioxanone and blends or other combinations thereof and equivalents thereof. Examples of non-absorbable materials include metals such as stainless steel, titanium, Nitinol, cobalt, alloys thereof, and equivalents thereof and polymeric materials such as non-absorbable polyesters, polyamides, polyolefins, polyurethanes, and polyacetals and equivalents thereof.

The anchors may be manufactured as a single piece using standard machining or molding techniques. Alternatively, discrete elements of the anchors can be manufactured separately and then connected together using conventional methods and materials. In such an embodiment, each discrete element may be made from the same or different materials.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture anchor assembly comprising:
   an anchor having a first passageway and an enclosed second passageway extending through at least a portion of the anchor;
   a suture comprising a proximal end and an opposing distal end, a portion of the suture between the proximal end and the distal end being formed into a loop, the loop being at least partially passed through the first passageway, at least one of the proximal end or the distal end of the suture being passed through the loop such that pulling on at least one of the proximal end or the distal end of the suture that is passed through the loop causes the suture to selectively lock against the anchor, a portion of the proximal end or the distal end of the suture that is passed through the loop passing through the enclosed second passageway before passing through the loop; and
   a retraction line threaded through the loop of the suture such that the application of tension by the retraction line on the loop causes the suture to selectively unlock from the anchor.

2. A suture anchor assembly as recited in claim 1, further comprising a third passageway extending through at least a portion of the anchor, a portion of the proximal end or the distal end of the suture that is not passed through the loop passing through the third passageway.

3. A suture anchor assembly as recited in claim 1, further comprising a channel recessed along the length of the anchor, the channel intersecting with the first passageway and the enclosed second passageway.

4. A suture anchor assembly as recited in claim 1, further comprising a second anchor, the suture being secured to the second anchor distal of the loop.

5. A suture anchor assembly comprising:
   an anchor having a first passageway and a spaced apart second passageway each extending through at least a portion of the anchor;
   a suture comprising a proximal end and an opposing distal end, a portion of the suture between the proximal end and the distal end passing through the first passageway and the second passageway so as to form a loop, the loop being coiled so as to form a closed loop, at least one of the proximal end or the distal end of the suture being passed through the loop such that pulling on at least one of the proximal end or distal end of the suture that is passed through the loop causes the suture to selectively lock against the anchor; and
   a retraction line threaded through the loop of the suture such that the application of tension by the retraction line on the loop causes the suture to selectively unlock from the anchor, at least one of the proximal end or the distal end of the suture and the retraction line passing through the closed loop.

6. The suture anchor assembly recited in claim 5, wherein the proximal end of at least one of the proximal end or the distal end of the suture is passed through the loop.

7. The suture anchor assembly recited in claim 5, further comprising a third passageway extending through the anchor, the suture passing through the third passageway prior to passing through the loop.

8. A suture anchor assembly comprising:
   an anchor comprising:
      a top surface and an opposing bottom surface;
      an elongated channel recessed into the bottom surface; and
      an enclosed first passageway and a spaced apart enclosed second passageway extending from the top surface to the channel;
   a suture comprising a proximal end and an opposing distal end, a portion of the suture between the proximal end and the distal end being formed into a loop, the loop being at least partially passed through the enclosed first passageway, at least one of the proximal end or the distal end of the suture being passed through the enclosed second passageway and then through the loop such that pulling on the proximal end or the distal end of the suture that is passed through the loop causes the suture to selectively lock against the anchor.

9. A suture anchor assembly as recited in claim 8, further comprising a retraction line threaded through the loop of the suture such that tension can be applied on the loop through the retraction line.

10. A suture anchor assembly as recited in claim 8, wherein the anchor further comprises a third passageway, wherein the proximal end or the distal end of the suture that is not passed through the loop is passed through the third passageway.

11. A suture anchor assembly as recited in claim 10, further comprising a second anchor, wherein the proximal end or the distal end of the suture that is not passed through the loop is secured to the second anchor.

12. A suture anchor assembly as recited in claim 11, further comprising a channel recessed on the anchor, the channel intersecting with the first passageway and the second passageway.

13. A suture anchor assembly comprising:
   a first anchor;
   a second anchor having a first passageway extending through at least a portion thereof;

a suture comprising a proximal end and an opposing distal end, a portion of the suture between the proximal end and the distal end being formed into a loop, the loop being passed into the first passageway, at least one of the proximal end or the distal end of the suture being passed through the loop, the suture being secured to the first anchor at a location distal of the loop;

a retraction line threaded through the loop of the suture such that tension can be applied to the loop through the retraction line; and a tubular needle having an interior surface and an exterior surface extending between a proximal end and an opposing distal end, the interior surface bounding a passage, a slot extending between the interior surface of the needle and the exterior surface of the needle and running from the distal end of the needle toward the proximal end thereof, the first anchor and the second anchor being slidably received in the passage of the tubular needle.

14. The suture anchor assembly as recited in claim 13, wherein the first anchor further comprises an outwardly projecting flexible prong.

15. The suture anchor assembly as recited in claim 13, wherein the second anchor further comprises a channel recessed on the second anchor, the channel intersecting with the first passageway.

16. The suture anchor assembly as recited in claim 13, further comprising a second passageway extending through at least a portion of the second anchor, the suture passing through the second passageway.

17. A suture anchor delivery system comprising:
a tubular needle having an interior surface and an exterior surface extending between a proximal end and an opposing distal end, the interior surface bounding a passage, a slot extending between the interior surface of the needle and the exterior surface of the needle and running from the distal end of the needle toward the proximal end thereof;
a first anchor comprising:
a body slidably received within the passage of the needle;
a neck extending from the body, the neck passing through the slot of the needle so that the neck outwardly projects beyond the exterior surface of the needle; and
a flexible prong projecting from at least a portion of the neck or the body and resiliently biasing against the interior surface of the needle; and
a suture secured to the first anchor.

18. The suture anchor delivery system as recited in claim 17, further comprising:
the suture comprising a proximal end and an opposing distal end; and
a second anchor slidably received within the passage of the needle, the second anchor having a first passageway extending through at least a portion thereof, wherein a portion of the suture between the proximal end and the distal end being formed into a loop, the loop being at least partially passed through the first passageway, at least one of the proximal end or the distal end of the suture being passed through the loop, the suture being secured to the first anchor at a location distal of the loop.

19. The suture anchor delivery system as recited in claim 18, further comprising a retraction line threaded through the loop of the suture such that tension can be applied to the loop through the retraction line.

20. The suture anchor delivery system as recited in claim 19, wherein the proximal end of the suture is passed through the loop.

21. The suture anchor delivery system as recited in claim 19, wherein both the proximal end and the distal end of the suture is passed through the loop.

22. The suture anchor delivery system as recited in claim 18, wherein the second anchor further comprises a channel recessed on the second anchor, the channel intersecting with the first passageway.

23. The suture anchor delivery system as recited in claim 22, wherein a portion of the suture and at least a portion of the retraction line travel continually in the passage of the needle from the loop of the suture toward the proximal end of the needle.

24. The suture anchor delivery system as recited in claim 18, further comprising a handle disposed at the proximal end of the tubular needle.

25. The suture anchor delivery system as recited in claim 24, further comprising a sleeve disposed over a proximal portion of the tubular needle, the sleeve operable within the handle to selectively advance the second anchor toward the distal end of the tubular needle.

26. A suture anchor delivery system comprising:
a tubular needle having an interior surface and an exterior surface extending between a proximal end and an opposing distal end, the interior surface bounding a passage, a slot extending between the interior surface of the needle and the exterior surface of the needle and running from the distal end of the needle toward the proximal end thereof;
a handle positioned at the proximal end of the needle;
a first anchor at least partially slidably disposed within the passage of the needle;
a second anchor at least partially slidably disposed within the passage of the needle proximal of the first anchor, the second anchor having a first passageway extending through at least a portion thereof so as to communicate with the passage of the needle; and
a suture comprising a proximal end and an opposing distal end, a portion of the suture between the proximal end and the distal end being formed into a loop, the loop being at least partially passed through the first passageway of the second anchor, at least one of the proximal end or the distal end of the suture being passed through the loop, a portion of the suture traveling continually in the passage of the needle from the loop of the suture to the handle.

27. A suture anchor delivery system as recited in claim 26, further comprising a retraction line treaded through the loop of the suture, at least a portion of the retraction line traveling continually in the passage of the needle from the loop of the suture to the handle.

28. The suture anchor delivery system as recited in claim 26, wherein a shoulder projects into the slot of the tubular needle so as to retain the first anchor within the passage of the needle.

29. The suture anchor delivery system as recited in claim 26, wherein the first anchor comprises a flexible prong resiliently biasing against the interior surface of the needle.

30. The suture anchor delivery system as recited in claim 26, further comprises a channel recessed on the second anchor, the channel intersecting with the first passageway.

31. The suture anchor delivery system as recited in claim 26, wherein a portion of the suture and at least a portion of the retraction line travel continually in the passage of the needle from the loop of the suture toward the proximal end of the needle.

32. The suture anchor delivery system as recited in claim 26, further comprising a sleeve disposed over a proximal portion of the tubular needle, the sleeve operable to selectively advance the second anchor toward the distal end of the tubular needle.

33. A method for securing a suture on an anchor wherein a suture comprises a proximal end and an opposing distal end, a portion of the suture between the proximal end and the distal end being formed into a loop, the loop being passed at least partially through a passageway formed on the anchor, at least one of the proximal end or the distal end of the suture being passed through the loop, the method comprising:
  while holding securely the proximal end or the distal end of the suture that is passed through the loop, pulling on a retention line passing through the loop of the suture so as to remove any unwanted slack from the suture distal of the loop by enlarging the loop;
  pulling on the proximal end or distal end of the suture that is passed through the loop so as to remove slack from the loop and selectively lock the suture to the anchor; and
  removing the retention line from the loop.

34. The method as recited in claim 33, further comprising pulling on the retention line to selectively unlock the suture from the anchor.

35. A method for repairing soft tissue comprising:
  placing a first anchor into soft tissue, a suture being connected to the first anchor;
  placing a second anchor into soft tissue at a distance from the first anchor, the suture passing through at least a portion of the second anchor and terminating at a free end; and
  pulling on a retraction line extending through a loop formed on the suture so as to decrease the length of suture between the first anchor and the second anchor while the first anchor and the second anchor are substantially retained in place.

36. The method as recited in claim 35, further comprising pulling on the free end of the suture so as to selectively lock the suture to the second anchor.

37. The method as recited in claim 36, further comprising pulling on the retraction line so as to selectively unlock the suture on the second anchor.

38. A suture anchor assembly comprising:
  an anchor having a first passageway, second passageway, and a third passageway each extending through at least a portion of the anchor;
  a suture comprising a proximal end and an opposing distal end, a portion of the suture between the proximal end and the distal end passing through the first passageway and the second passageway so as to form a loop, at least one of the proximal end or the distal end of the suture being passed through the loop such that pulling on at least one of the proximal end or distal end of the suture that is passed through the loop causes the suture to selectively lock against the anchor, the suture also passing through the third passageway prior to passing through the loop; and
  a retraction line threaded through the loop of the suture such that the application of tension by the retraction line on the loop causes the suture to selectively unlock from the anchor.

39. A suture anchor assembly comprising:
  a first anchor having an outwardly projecting flexible prong;
  a second anchor having a first passageway extending through at least a portion thereof;
  a suture comprising a proximal end and an opposing distal end, a portion of the suture between the proximal end and the distal end being formed into a loop, the loop being passed into the first passageway, at least one of the proximal end or the distal end of the suture being passed through the loop, the suture being secured to the first anchor at a location distal of the loop; and
  a retraction line threaded through the loop of the suture such that tension can be applied to the loop through the retraction line.

* * * * *

UNITED STATES PATENT AND TRADEMARK OFFICE
CERTIFICATE OF CORRECTION

PATENT NO.        : 6,972,027 B2                                   Page 1 of 1
APPLICATION NO. : 10/180901
DATED             : December 6, 2005
INVENTOR(S)       : T. Wade Fallin et al.

It is certified that error appears in the above-identified patent and that said Letters Patent is hereby corrected as shown below:

Column 5, line 63 (detailed description) ADD --.-- after "can be divided"

Column 6, line 56 (detailed description) Delete "were" and ADD --where--

Column 12, line 22, (claim 6) Delete "at least one of the proximal end or the distal end of"

Column 14, line 51, Delete "treaded" and ADD --threaded--

Column 14, line 64, Delete "comprises" and ADD --comprising--

Signed and Sealed this

Tenth Day of October, 2006

JON W. DUDAS
*Director of the United States Patent and Trademark Office*